US012649743B2

(12) United States Patent
Li et al.

(10) Patent No.: US 12,649,743 B2
(45) Date of Patent: Jun. 9, 2026

(54) TRICYCLIC FUSED HETEROCYCLIC PDE3/4 DUAL INHIBITOR AND USE THEREOF

(71) Applicant: XIZANG HAISCO PHARMACEUTICAL CO., LTD., Lhoka (CN)

(72) Inventors: Yao Li, Lhoka (CN); Guobiao Zhang, Lhoka (CN); Xiaobo Zhang, Lhoka (CN); Yaming Zhang, Lhoka (CN); Linjie Yan, Lhoka (CN); Pingming Tang, Lhoka (CN); Yan Yu, Lhoka (CN); Chen Zhang, Lhoka (CN); Pangke Yan, Lhoka (CN)

(73) Assignee: XIZANG HAISCO PHARMACEUTICAL CO., LTD., Lhoka (CN)

( * ) Notice: Subject to any disclaimer, the term of this patent is extended or adjusted under 35 U.S.C. 154(b) by 0 days.

(21) Appl. No.: 19/270,230

(22) Filed: Jul. 15, 2025

(65) Prior Publication Data

US 2025/0340555 A1 Nov. 6, 2025

Related U.S. Application Data

(63) Continuation of application No. 18/720,168, filed as application No. PCT/CN2022/138629 on Dec. 13, 2022.

(30) Foreign Application Priority Data

Dec. 14, 2021 (CN) ......................... 202111527081.7
Feb. 9, 2022 (CN) ......................... 202210121834.2

(51) Int. Cl.
*C07D 471/04* (2006.01)
*A61K 31/519* (2006.01)
*A61P 11/00* (2006.01)

(52) U.S. Cl.
CPC .......... *C07D 471/04* (2013.01); *A61K 31/519* (2013.01); *A61P 11/00* (2018.01)

(58) Field of Classification Search
CPC ...... C07D 471/04; A61K 31/519; A61P 11/00
See application file for complete search history.

(56) References Cited

U.S. PATENT DOCUMENTS

| | | | | |
|---|---|---|---|---|
| 6,221,335 B1 * | 4/2001 | Foster | C07B 59/002 424/1.81 |
| 6,603,008 B1 * | 8/2003 | Ando | A61P 7/04 546/271.4 |
| 6,794,391 B2 | 9/2004 | Oxford et al. | |
| 11,993,596 B2 | 5/2024 | Luo et al. | |
| 2007/0082929 A1 * | 4/2007 | Gant | A61P 43/00 546/273.7 |
| 2007/0197695 A1 * | 8/2007 | Potyen | C08K 5/55 524/110 |
| 2024/0217974 A1 | 7/2024 | Li et al. | |

FOREIGN PATENT DOCUMENTS

| | | | |
|---|---|---|---|
| CN | 1348453 | A | 5/2002 |
| EP | 3822272 | A1 | 5/2021 |
| EP | 4610257 | A1 | 9/2025 |
| GB | 1597717 | A | 9/1981 |
| WO | WO 00/58308 | * | 10/2000 |
| WO | WO2000058308 | A1 | 10/2000 |
| WO | WO2003105902 | A1 | 12/2003 |
| WO | WO2016128742 | A1 | 8/2016 |
| WO | WO2018020249 | A1 | 2/2018 |
| WO | WO2020011254 | A1 | 1/2020 |
| WO | WO2021143843 | A1 | 7/2021 |
| WO | WO-2023109802 | A1 | 6/2023 |

OTHER PUBLICATIONS

CDC https://www.cdc.gov/copd/about/index.html, 2024 (Year: 2024).*
Jayasooriya, www.thelancet.com/respiratory vol. Aug. 13, 2025, p. 725-738 (Year: 2025).*
Mayo Clinic https://www. mayoclinic.org/diseases-conditions/asthma/symptoms-causes/syc-20369653 (Year: 2025).*
Dyck et al. (Journal of Neurochemistry vol. 46, Issue 2, pp. 399-404 (1986) (Year: 1986).*
Wolen (Journal of Clinical Pharmacology, 1986, vol. 26, pp. 419-424 (Year: 1986).*
Schneider et al., Pharmacokinetic and Metabolic Profile of Deutetrabenazine (TEV-50717) Compared With Tetrabenazine in Healthy Volunteers, Clin Transl Sci., 13(4):707-717, 2020.

(Continued)

*Primary Examiner* — Umamaheswari Ramachandran
(74) *Attorney, Agent, or Firm* — Wilson Sonsini Goodrich & Rosati

(57) ABSTRACT

Disclosed are a tricyclic fused heterocyclic compound having a PDE3/4 dual inhibitory effect represented by formula (I), a stereoisomer, a solvate, or a pharmaceutically acceptable salt thereof, and the use thereof in the preparation of a drug for treating/preventing PDE3/4-mediated diseases. Each group in formula (I) is as defined in the description.

(I)

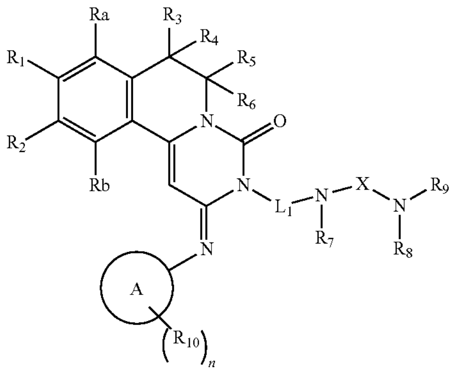

18 Claims, No Drawings

(56) References Cited

OTHER PUBLICATIONS

Calzetta et al., Effect of the Mixed Phosphodiesterase 3/4 Inhibitor RPL554 on Human Isolated Bronchial Smooth Muscle Tone, J Pharmacol Exp Ther., 346(3):414-23, 2023.
Crestey, Francois. et al. Design, synthesis, and biological evaluation of Erythrina alkaloid analogues as neuronal nicotinic acetylcholine receptor antagonists. Journal of medicinal chemistry 56(23):9673-9682 (2013).
EP22906547.9 Extended European Search Report dated Sep. 16, 2025.
EP22906547.9 Third Party Observations dated Mar. 25, 2025.
EP22906547.9 Third Party Observations dated Oct. 27, 2025.
EP25188978.8 Extended European Search Report dated Sep. 16, 2025.
EP25188978.8 Office Action dated Nov. 21, 2025.
Lal, B. et al., Trequinsin, a potent new antihypertensive vasodilator in the series of 2-(arylimino)-3-alkyl-9,10-dimethoxy-3,4,6,7-tetrahydro-2H-pyrimido[6, 1-a]isoquinolin-4-ones, Journal of Medicinal Chemistry, vol. 27, 11(1984):1470-80.
PCT/CN2022/138629 International Search Report and Written Opinion dated Mar. 6, 2023.

* cited by examiner

TRICYCLIC FUSED HETEROCYCLIC PDE3/4 DUAL INHIBITOR AND USE THEREOF

This application is a continuation of U.S. application Ser. No. 18/720,168 filed Jun. 14, 2024, which application is a U.S. National Stage Application of PCT Application No. PCT/CN2022/138629 filed Dec. 13, 2022, which application claims priority to the filing date of Chinese Application No. 202210121834.2 filed Feb. 9, 2022, and Chinese Application No. 202111527081.7 filed Dec. 14, 2021.

TECHNICAL FIELD

The present invention relates to a PDE3/4 dual inhibitor and the use thereof in the preparation of a drug for the treatment of COPD and asthma.

BACKGROUND ART

COPD (chronic obstructive pulmonary disease) is a group of lung diseases characterized by airflow limitation that is not fully reversible and is progressive. It mainly affects the lungs and is the most common chronic killer of lung health. The incidence and mortality rates of COPD remain high. On the one hand, COPD is difficult to diagnose in its early stages and its onset is often hidden. Once the clinical manifestations of COPD appear, they often indicate a gradual decline in the patient's overall health and a gradual increase in respiratory symptoms. On the other hand, COPD is currently incurable, and drugs for treating COPD mainly rely on bronchodilators that can regulate airway smooth muscles. Such drugs can only relieve the symptoms and delay the worsening of the disease, but they only treat the symptoms and not the underlying cause. COPD has a long disease course, and patients often require frequent medical visits, hospitalization for acute exacerbations and long-term care, consuming large amounts of healthcare resources and becoming a challenging global disease burden. Therefore, new drugs for treating COPD need to be developed against different targets to meet various clinical needs.

Phosphodiesterase (PDE) is a member of a superfamily of enzyme systems that includes 11 families, each of which is involved in different signaling pathways and regulates different physiological processes. Studies have shown that PDE3 is associated with the contraction of smooth muscles in the respiratory system, while PDE4 plays a key role in the inflammatory response caused by immune cells. Given the clinical limitations of selective inhibitors of either PDE3 or PDE4, a PDE3/4 dual inhibitor appears to be a more attractive approach to target key pathological features of COPD and asthma. Currently, there is evidence that a PDE3/4 dual inhibitor has synergistic inhibitory effects, including synergistic anti-inflammatory and bronchodilatory effects. WO 2000058308 A1 reported that the compound RPL554 has long-acting bronchodilatory and anti-inflammatory effects, but the drug has poor solubility and high plasma clearance and is suitable for inhalation administration; in addition, biological activity data show that its PDE4 inhibitory activity is unsatisfactory, which may lead to suboptimal anti-inflammatory effects. Therefore, a PDE3/4 dual inhibitor is still worthy of further study.

SUMMARY OF THE INVENTION

The present invention provides a compound represented by formula (I) or formula (II), or a stereoisomer, solvate, or pharmaceutically acceptable salt thereof, wherein the compound has the advantages of good activity, favorable physical and chemical properties for preparation, high bioavailability, and low toxic and side effects.

Regarding the compound represented by formula (I) or formula (II), or the stereoisomer, solvate, or pharmaceutically acceptable salt thereof,

I

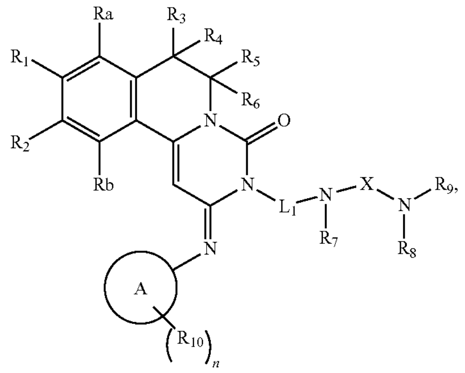

II

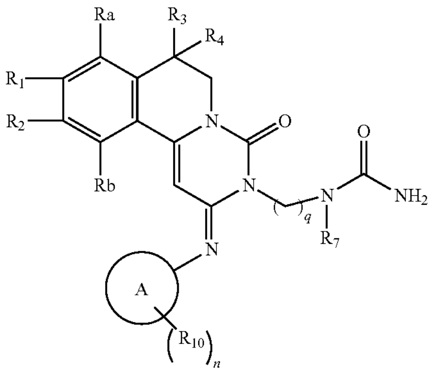

wherein $R_1$, $R_2$, $R_a$ and $R_b$ are independently H, deuterium, halogen, CN, OH, $NH_2$, —$NHC_{1-4}$ alkyl, —$N(C_{1-4}$ alkyl$)_2$, —$OC_{1-4}$ alkyl, —$O(CH_2)_mC_{3-6}$ cycloalkyl, —$O(CH_2)_m$ phenyl, —$O(CH_2)_m$-4- to 7-membered heterocycloalkyl containing 1-3 heteroatoms selected from N, S or O, —$O(CH_2)_m$-5- to 6-membered heteroaryl containing 1-3 heteroatoms selected from N, S or O, $C_{1-4}$ alkyl, —$(CH_2)_mC_{3-6}$ cycloalkyl, —$(CH_2)_m$ phenyl, —$(CH_2)_m$-4- to 7-membered heterocycloalkyl containing 1-3 heteroatoms selected from N, S or O, or —$(CH_2)_m$-5- to 6-membered heteroaryl containing 1-3 heteroatoms selected from N, S or O, wherein the alkyl, phenyl, cycloalkyl, heterocycloalkyl and heteroaryl are optionally further substituted with 1-3 groups selected from deuterium, halogen, $C_{1-4}$ alkyl, $C_{2-4}$ alkenyl, $C_{2-4}$ alkynyl, $C_{1-4}$ alkoxy, deuterated $C_{1-4}$ alkyl, deuterated $C_{1-4}$ alkoxy, halo $C_{1-4}$ alkoxy, CN, $NH_2$, —$NHC_{1-4}$ alkyl, —$N(C_{1-4}$ alkyl) 2 and OH;

in some embodiments, $R_1$, $R_2$, $R_a$ and $R_b$ are independently H, deuterium, halogen, CN, OH, $NH_2$, —$NHC_{1-4}$ alkyl, —$N(C_{1-4}$ alkyl$)_2$, —$OC_{1-4}$ alkyl, —$O(CH_2)_mC_{3-6}$ cycloalkyl, —$O(CH_2)_m$-4- to 7-membered heterocycloalkyl containing 1-3 heteroatoms selected from N, S or O, $C_{1-4}$ alkyl, —$(CH_2)_mC_{3-6}$ cycloalkyl, or —$(CH_2)_m$-4- to 7-membered heterocycloalkyl containing 1-3 heteroatoms selected from N, S or O, wherein the alkyl, cycloalkyl and heterocycloalkyl are optionally further substituted with 1-3 groups selected from deuterium, halogen, $C_{1-4}$ alkyl, $C_{2-4}$ alkenyl, $C_{2-4}$ alkynyl, $C_{1-4}$ alkoxy, deuterated $C_{1-4}$ alkyl, deuterated $C_{1-4}$ alkoxy and halo $C_{1-4}$ alkoxy;

in some embodiments, $R_1$, $R_2$, $R_a$ and $R_b$ are independently H, deuterium, halogen, CN, OH, —$OC_{1-4}$ alkyl, —$O(CH_2)_mC_{3-6}$ cycloalkyl, $C_{1-4}$ alkyl, or —$(CH_2)_mC_{3-6}$ cycloalkyl, wherein the alkyl and cycloalkyl are optionally further substituted with 1-3 groups selected from deuterium, halogen, $C_{1-4}$ alkyl, $C_{1-4}$ alkoxy, deuterated $C_{1-4}$ alkyl, deuterated $C_{1-4}$ alkoxy and halo $C_{1-4}$ alkoxy;

in some embodiments, $R_1$, $R_2$, $R_a$ and $R_b$ are independently H, methoxy, ethoxy, propoxy, isopropoxy, —$O(CH_2)_m$ cyclopropyl, methyl, ethyl, propyl, isopropyl or —$(CH_2)_m$ cyclopropyl, wherein the methoxy, ethoxy, propoxy, isopropoxy, cyclopropyl, methyl, ethyl, propyl, isopropyl and cyclopropyl are optionally further substituted with 1-3 groups selected from deuterium, F, Cl, Br, I, methyl, ethyl, propyl, isopropyl, methoxy, ethoxy, propoxy, deuterated methyl, deuterated ethyl, deuterated propyl, deuterated methoxy, deuterated ethoxy, deuterated propoxy, halomethoxy, haloethoxy and halopropoxy;

optionally, $R_1$ and $R_2$ together with the atom to which they are attached form a 5- to 7-membered heterocycle containing 1-3 heteroatoms selected from N, S or O, or a $C_{4-7}$ carbocycle, wherein the heterocycle and carbocycle are optionally substituted with 1-3 groups selected from deuterium, halogen, $C_{1-4}$ alkyl, halo $C_{1-4}$ alkyl, $C_{2-4}$ alkenyl, $C_{2-4}$ alkynyl, $C_{1-4}$ alkoxy, deuterated $C_{1-4}$ alkoxy and halo $C_{1-4}$ alkoxy;

in some embodiments, $R_1$ and $R_2$ together with the atom to which they are attached form a 5- to 6-membered heterocycle containing 1-3 heteroatoms selected from N, S or O, or a $C_{5-6}$ carbocycle, wherein the heterocycle and carbocycle are optionally substituted with 1-3 groups selected from deuterium, halogen, $C_{1-4}$ alkyl, halo $C_{1-4}$ alkyl, $C_{1-4}$ alkoxy, deuterated $C_{1-4}$ alkoxy and halo $C_{1-4}$ alkoxy;

in some embodiments, $R_1$ and $R_2$ together with the atom to which they are attached form a 5- to 6-membered heterocycle containing 1-3 heteroatoms selected from N, S or O, or a $C_{5-6}$ carbocycle, wherein the heterocycle and carbocycle are optionally substituted with 1-3 groups selected from deuterium, halogen, $C_{1-4}$ alkyl, halo $C_{1-4}$ alkyl and $C_{1-4}$ alkoxy;

in some embodiments, $R_1$ and $R_2$ together with the atom to which they are attached form

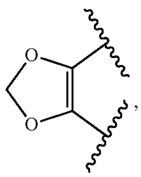 [SMILES: *C1=C(*)OCO1], and are optionally substituted with 1-2 groups selected from deuterium, F, Cl, Br, I, methyl, ethyl, propyl, methoxy, ethoxy, propoxy, halomethyl, haloethyl and halopropyl;

$R_3$, $R_4$, $R_5$ and $R_6$ are independently H, deuterium, halogen, $C_{1-4}$ alkyl and —$(CH_2)_mC_{3-6}$ cycloalkyl, wherein the alkyl and cycloalkyl are optionally substituted with 1-3 groups selected from deuterium, halogen, CN and $NH_2$;

in some embodiments, $R_3$, $R_4$, $R_5$ and $R_6$ are independently H, deuterium, halogen and $C_{1-4}$ alkyl, wherein the alkyl is optionally substituted with 1-3 groups selected from deuterium, halogen, CN and $NH_2$;

in some embodiments, $R_3$ and $R_4$ are independently H, deuterium, halogen and $C_{1-4}$ alkyl, wherein the alkyl is optionally substituted with 1-3 groups selected from deuterium, F, Cl, Br and I; $R_5$ and $R_6$ are independently H;

in some embodiments, $R_3$ and $R_4$ are independently H, deuterium, F, Cl, Br, I, methyl, ethyl or propyl, wherein the methyl, ethyl or propyl is optionally substituted with 1-3 groups selected from deuterium, F, Cl, Br and I; $R_5$ and $R_6$ are independently H;

optionally, $R_3$ and $R_4$, or $R_5$ and $R_6$ together with the carbon atom to which they are attached form $C_{3-6}$ cycloalkyl;

X is CO or $SO_2$; in some embodiments, X is CO;

ring A is phenyl, a $C_{9-10}$ fused carbocycle or 5- to 6-membered heteroaryl containing 1-3 heteroatoms selected from N, S or O;

in some embodiments, ring A is phenyl,

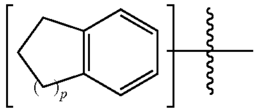

(the attachment site is any ring atom on the ring that conforms to the rules of chemical bonding), pyridyl, pyrimidyl, thienyl, thiazolyl, isothiazolyl, oxazolyl or isoxazolyl;

in some embodiments, ring A is phenyl,

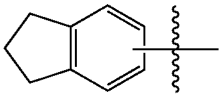

(the attachment site is any ring atom on the ring that conforms to the rules of chemical bonding), thienyl, thiazolyl, isothiazolyl, oxazolyl or isoxazolyl;

in some embodiments, ring A is phenyl,

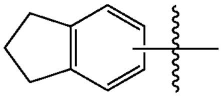

(the attachment site is any ring atom on the ring that conforms to the rules of chemical bonding), thienyl or thiazolyl;

$L_1$ is $C_{1-6}$ alkylene, wherein the alkylene is optionally substituted with 1-3 groups selected from deuterium, halogen, $C_{2-4}$ alkenyl, $C_{2-4}$ alkynyl, $C_{1-4}$ alkoxy, deuterated $C_{1-4}$ alkoxy and halo $C_{1-4}$ alkoxy;

in some embodiments, $L_1$ is $C_{2-4}$ alkylene, wherein the alkylene is optionally substituted with 1-3 groups selected from deuterium, halogen, $C_{1-4}$ alkoxy, deuterated $C_{1-4}$ alkoxy and halo $C_{1-4}$ alkoxy;

in some embodiments, $L_1$ is $C_{2-4}$ alkylene;

$R_7$ is H, $C_{1-4}$ alkyl or $—(CH_2)_mC_{3-6}$ cycloalkyl, wherein the alkyl and cycloalkyl are optionally substituted with 1-3 groups selected from deuterium, halogen, $C_{2-4}$ alkenyl, $C_{2-4}$ alkynyl, $C_{1-4}$ alkoxy, deuterated $C_{1-4}$ alkoxy and halo $C_{1-4}$ alkoxy;

in some embodiments, $R_7$ is H or $C_{1-4}$ alkyl, wherein the alkyl is optionally substituted with 1-3 groups selected from deuterium, halogen, $C_{1-4}$ alkoxy, deuterated $C_{1-4}$ alkoxy and halo $C_{1-4}$ alkoxy;

in some embodiments, $R_7$ is H or $C_{1-3}$ alkyl, wherein the alkyl is optionally substituted with 1-3 groups selected from deuterium, halogen, $C_{1-4}$ alkoxy, deuterated $C_{1-4}$ alkoxy and halo $C_{1-4}$ alkoxy;

in some embodiments, $R_7$ is H, methyl, ethyl, propyl or isopropyl, wherein the methyl, ethyl, propyl or isopropyl is optionally substituted with 1-3 groups selected from deuterium, F, Cl, Br, I, methoxy, ethoxy, propoxy, deuterated methyl, deuterated ethyl, deuterated propyl, deuterated methoxy, deuterated ethoxy, deuterated propoxy, halomethoxy, haloethoxy and halopropoxy;

$R_8$ and $R_9$ are independently H, $C_{1-4}$ alkyl and $C_{3-6}$ cycloalkyl;

in some embodiments, $R_8$ and $R_9$ are independently H;

optionally, $R_8$ and $R_9$ together with the N atom to which they are attached form a 5- to 6-membered heterocycle containing 1-3 heteroatoms selected from N, S or O, wherein the heterocycle is optionally substituted with 1-3 groups selected from ═O, deuterium, halogen, $C_{1-4}$ alkyl, $C_{1-4}$ alkoxy, deuterated $C_{1-4}$ alkoxy and halo $C_{1-4}$ alkoxy;

in some embodiments, $R_8$ and $R_9$ together with the N atom to which they are attached form a 5- to 6-membered heterocycle containing 1-3 heteroatoms selected from N, S or O, wherein the heterocycle is optionally substituted with 1-3 groups selected from ═O, deuterium, halogen, $C_{1-4}$ alkyl and $C_{1-4}$ alkoxy;

each $R_{10}$ is independently H, halogen, CN, $NH_2$, $—NHC_{1-4}$ alkyl, $—N(C_{1-4}\ alkyl)_2$, OH, $C_{1-4}$ alkyl, $C_{2-4}$ alkenyl, $C_{2-4}$ alkynyl, $—(CH_2)_m—C_{3-6}$ cycloalkyl, $—O—C_{3-6}$ cycloalkyl or $C_{1-4}$ alkoxy, wherein the alkyl, alkenyl, alkynyl, cycloalkyl and alkoxy are optionally substituted with 1-3 groups selected from deuterium, halogen, $C_{1-4}$ alkyl, $C_{2-4}$ alkenyl, $C_{2-4}$ alkynyl, CN, $NH_2$, $—NHC_{1-4}$ alkyl, $—N(C_{1-4}\ alkyl)_2$ and OH;

in some embodiments, each $R_{10}$ is independently H, halogen, CN, $C_{1-4}$ alkyl, $C_{2-4}$ alkenyl, $C_{2-4}$ alkynyl, $C_{3-6}$ cycloalkyl or $C_{1-4}$ alkoxy, wherein the alkyl, alkenyl, alkynyl, cycloalkyl and alkoxy are optionally substituted with 1-3 groups selected from deuterium, halogen, $C_{1-4}$ alkyl and CN;

in some embodiments, each $R_{10}$ is independently H, halogen, CN, $C_{1-4}$ alkyl, $C_{2-4}$ alkenyl, $C_{2-4}$ alkynyl, $C_{3-4}$ cycloalkyl or $C_{1-4}$ alkoxy, wherein the alkyl, alkenyl, alkynyl, cycloalkyl and alkoxy are optionally substituted with 1-3 groups selected from deuterium, halogen, $C_{1-4}$ alkyl and CN;

in some embodiments, each $R_{10}$ is independently H, F, Cl, Br, I, CN, methyl, ethyl, propyl, isopropyl, n-butyl, isobutyl, ethenyl, propenyl, allyl, ethynyl, propynyl, cyclopropyl, cyclobutyl, methoxy, ethoxy or propoxy, wherein the methyl, ethyl, propyl, isopropyl, n-butyl, isobutyl, ethenyl, propenyl, allyl, ethynyl, propynyl, cyclopropyl, cyclobutyl, methoxy, ethoxy and propoxy are optionally substituted with 1-3 groups selected from deuterium, F, Cl, Br, I, methyl, ethyl, propyl and CN;

n is 0, 1, 2, 3 or 4;

in some embodiments, n is 0, 1, 2 or 3;

each m is independently 0, 1, 2, 3 or 4;

in some embodiments, each m is independently 0, 1, 2 or 3;

q is 2 or 3;

provided that when

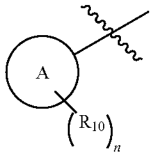

is

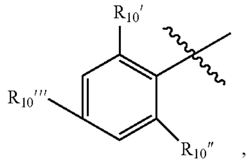

, $R_{10}'$, $R_{10}''$ and $R_{10}'''$ are as defined in $R_{10}$, and the compound satisfies that:

(iv) $R_1$ and $R_2$ are not both methoxy; or (v) $R_3$, $R_4$, $R_5$ and $R_6$ are not all H; or (vi) $R_{10}'''$ is not H or methyl.

More specifically, the first technical solution of the present invention provides a compound represented by formula (I), or a stereoisomer, solvate, or pharmaceutically acceptable salt thereof,

I

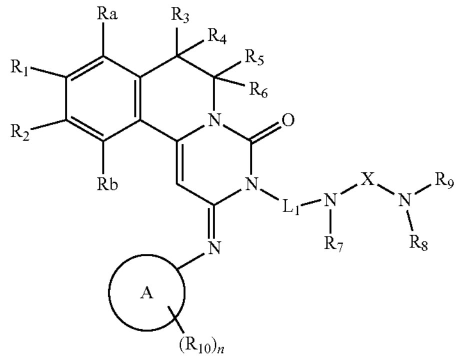

wherein $R_1$, $R_2$, $R_a$ and $R_b$ are independently H, deuterium, halogen, CN, OH, $NH_2$, $—NHC_{1-4}$ alkyl, $—N(C_{1-4}\ alkyl)_2$, $—OC_{1-4}$ alkyl, $—O(CH_2)_mC_{3-6}$ cycloalkyl, $—O(CH_2)_m$ phenyl, $—O(CH_2)_m$-4- to 7-membered heterocycloalkyl containing 1-3 heteroatoms selected from N, S or O, $—O(CH_2)_m$-5- to 6-membered heteroaryl containing 1-3 heteroatoms selected from N, S or O, $C_{1-4}$ alkyl, $—(CH_2)_mC_{3-6}$ cycloalkyl, $—(CH_2)_m$ phenyl, $—(CH_2)_m$-4- to 7-membered heterocycloalkyl containing 1-3 heteroatoms selected from N, S or O, or $—(CH_2)_m$-5- to 6-membered heteroaryl containing 1-3 heteroatoms selected from N, S or O, wherein the alkyl, phenyl, cycloalkyl, heterocycloalkyl and heteroaryl are optionally further substituted with 1-3 groups selected from deuterium, halogen, $C_{1-4}$ alkyl, $C_{2-4}$ alkenyl, $C_{2-4}$ alkynyl, $C_{1-4}$ alkoxy, deuterated $C_{1-4}$ alkyl, deuterated $C_{1-4}$ alkoxy, halo $C_{1-4}$ alkoxy, CN, $NH_2$, $—NHC_{1-4}$ alkyl, $—N(C_{1-4}\ alkyl)_2$ and OH;

optionally, $R_1$ and $R_2$ together with the atom to which they are attached form a 5- to 7-membered heterocycle containing 1-3 heteroatoms selected from N, S or O, or a $C_{4-7}$ carbocycle, wherein the heterocycle and carbocycle are optionally substituted with 1-3 groups selected from deuterium, halogen, $C_{1-4}$ alkyl, halo $C_{1-4}$ alkyl, $C_{2-4}$ alkenyl, $C_{2-4}$ alkynyl, $C_{1-4}$ alkoxy, deuterated $C_{1-4}$ alkoxy and halo $C_{1-4}$ alkoxy;

$R_3$, $R_4$, $R_5$ and $R_6$ are independently H, deuterium, halogen, $C_{1-4}$ alkyl and $-(CH_2)_mC_{3-6}$ cycloalkyl, wherein the alkyl and cycloalkyl are optionally substituted with 1-3 groups selected from deuterium, halogen, CN and $NH_2$;

optionally, $R_3$ and $R_4$, or $R_5$ and $R_6$ together with the carbon atom to which they are attached form $C_{3-6}$ cycloalkyl;

X is CO or $SO_2$;

ring A is phenyl, a $C_{9-10}$ fused carbocycle or 5- to 6-membered heteroaryl containing 1-3 heteroatoms selected from N, S or O;

$L_1$ is $C_{1-6}$ alkylene, wherein the alkylene is optionally substituted with 1-3 groups selected from deuterium, halogen, $C_{2-4}$ alkenyl, $C_{2-4}$ alkynyl, $C_{1-4}$ alkoxy, deuterated $C_{1-4}$ alkoxy and halo $C_{1-4}$ alkoxy;

$R_7$ is H, $C_{1-4}$ alkyl or $-(CH_2)_mC_{3-6}$ cycloalkyl, wherein the alkyl and cycloalkyl are optionally substituted with 1-3 groups selected from deuterium, halogen, $C_{2-4}$ alkenyl, $C_{2-4}$ alkynyl, $C_{1-4}$ alkoxy, deuterated $C_{1-4}$ alkoxy and halo $C_{1-4}$ alkoxy;

$R_8$ and $R_9$ are independently H, $C_{1-4}$ alkyl and $C_{3-6}$ cycloalkyl;

optionally, $R_8$ and $R_9$ together with the N atom to which they are attached form a 5- to 6-membered heterocycle containing 1-3 heteroatoms selected from N, S or O, wherein the heterocycle is optionally substituted with 1-3 groups selected from =O, deuterium, halogen, $C_{1-4}$ alkyl, $C_{1-4}$ alkoxy, deuterated $C_{1-4}$ alkoxy and halo $C_{1-4}$ alkoxy;

each $R_{10}$ is independently H, halogen, CN, $NH_2$, $-NHC_{1-4}$ alkyl, $-N(C_{1-4}$ alkyl$)_2$, OH, $C_{1-4}$ alkyl, $C_{2-4}$ alkenyl, $C_{2-4}$ alkynyl, $-(CH_2)_m-C_{3-6}$ cycloalkyl, $-O-C_{3-6}$ cycloalkyl or $C_{1-4}$ alkoxy, wherein the alkyl, alkenyl, alkynyl, cycloalkyl and alkoxy are optionally substituted with 1-3 groups selected from deuterium, halogen, $C_{1-4}$ alkyl, $C_{2-4}$ alkenyl, $C_{2-4}$ alkynyl, CN, $NH_2$, $-NHC_{1-4}$ alkyl, $-N(C_{1-4}$ alkyl$)_2$ and OH;

n is 0, 1, 2, 3 or 4;

each m is independently 0, 1, 2, 3 or 4;

provided that when

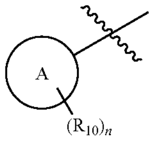

is

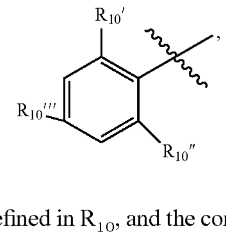

, $R_{10}'$, $R_{10}''$ and $R_{10}'''$ are as defined in $R_{10}$, and the compound satisfies that:

(vii) $R_1$ and $R_2$ are not both methoxy; or (viii) $R_3$, $R_4$, $R_5$ and $R_6$ are not all H; or (ix) $R_{10}'''$ is not H or methyl.

More specifically, the second technical solution of the present invention provides a compound represented by formula I, or a stereoisomer, solvate, or pharmaceutically acceptable salt thereof, wherein $R_1$, $R_2$, $R_a$ and $R_b$ are independently H, deuterium, halogen, CN, OH, $NH_2$, $-NHC_{1-4}$ alkyl, $-N(C_{1-4}$ alkyl$)_2$, $-OC_{1-4}$ alkyl, $-O(CH_2)_mC_{3-6}$ cycloalkyl, $-O(CH_2)_m$-4- to 7-membered heterocycloalkyl containing 1-3 heteroatoms selected from N, S or O, $C_{1-4}$ alkyl, $-(CH_2)_mC_{3-6}$ cycloalkyl, or $-(CH_2)_m$-4- to 7-membered heterocycloalkyl containing 1-3 heteroatoms selected from N, S or O, wherein the alkyl, cycloalkyl and heterocycloalkyl are optionally further substituted with 1-3 groups selected from deuterium, halogen, $C_{1-4}$ alkyl, $C_{2-4}$ alkenyl, $C_{2-4}$ alkynyl, $C_{1-4}$ alkoxy, deuterated $C_{1-4}$ alkyl, deuterated $C_{1-4}$ alkoxy and halo $C_{1-4}$ alkoxy;

optionally, $R_1$ and $R_2$ together with the atom to which they are attached form a 5- to 6-membered heterocycle containing 1-3 heteroatoms selected from N, S or O, or a $C_{5-6}$ carbocycle, wherein the heterocycle and carbocycle are optionally substituted with 1-3 groups selected from deuterium, halogen, $C_{1-4}$ alkyl, halo $C_{1-4}$ alkyl, $C_{1-4}$ alkoxy, deuterated $C_{1-4}$ alkoxy and halo $C_{1-4}$ alkoxy;

$R_3$, $R_4$, $R_5$ and $R_6$ are independently H, deuterium, halogen and $C_{1-4}$ alkyl, wherein the alkyl is optionally substituted with 1-3 groups selected from deuterium, halogen, CN and $NH_2$;

ring A is phenyl,

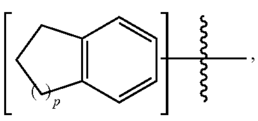

, pyridyl, pyrimidyl, thienyl, thiazolyl, isothiazolyl, oxazolyl or isoxazolyl;

$L_1$ is $C_{2-4}$ alkylene, wherein the alkylene is optionally substituted with 1-3 groups selected from deuterium, halogen, $C_{1-4}$ alkoxy, deuterated $C_{1-4}$ alkoxy and halo $C_{1-4}$ alkoxy;

$R_7$ is H or $C_{1-4}$ alkyl, wherein the alkyl is optionally substituted with 1-3 groups selected from deuterium, halogen, $C_{1-4}$ alkoxy, deuterated $C_{1-4}$ alkoxy and halo $C_{1-4}$ alkoxy;

$R_8$ and $R_9$ are independently H, $C_{1-4}$ alkyl and $C_{3-6}$ cycloalkyl;

optionally, $R_8$ and $R_9$ together with the N atom to which they are attached form a 5- to 6-membered heterocycle containing 1-3 heteroatoms selected from N, S or O, wherein the heterocycle is optionally substituted with 1-3 groups selected from =O, deuterium, halogen, $C_{1-4}$ alkyl and $C_{1-4}$ alkoxy;

each $R_{10}$ is independently H, halogen, CN, $C_{1-4}$ alkyl, $C_{2-4}$ alkenyl, $C_{2-4}$ alkynyl, $C_{3-6}$ cycloalkyl or $C_{1-4}$ alkoxy, wherein the alkyl, alkenyl, alkynyl, cycloalkyl and alkoxy are optionally substituted with 1-3 groups selected from deuterium, halogen, $C_{1-4}$ alkyl and CN;

p is 1 or 2;

the rest is as described in the first technical solution.

More specifically, the third technical solution of the present invention provides a compound represented by formula I, or a stereoisomer, solvate, or pharmaceutically acceptable salt thereof, wherein the compound has a structure of formula II:

II

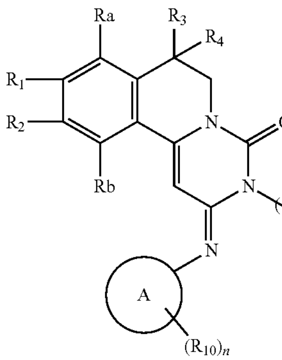

wherein $R_1$, $R_2$, $R_a$ and $R_b$ are independently H, deuterium, halogen, CN, OH, $—OC_{1-4}$ alkyl, $—O(CH_2)_mC_{3-6}$ cycloalkyl, $C_{1-4}$ alkyl, or $—(CH_2)_mC_{3-6}$ cycloalkyl, wherein the alkyl and cycloalkyl are optionally further substituted with 1-3 groups selected from deuterium, halogen, $C_{1-4}$ alkyl, $C_{1-4}$ alkoxy, deuterated $C_{1-4}$ alkyl, deuterated $C_{1-4}$ alkoxy and halo $C_{1-4}$ alkoxy;

optionally, $R_1$ and $R_2$ together with the atom to which they are attached form a 5- to 6-membered heterocycle containing 1-3 heteroatoms selected from N, S or O, or a $C_{5-6}$ carbocycle, wherein the heterocycle and carbocycle are optionally substituted with 1-3 groups selected from deuterium, halogen, $C_{1-4}$ alkyl, halo $C_{1-4}$ alkyl and $C_{1-4}$ alkoxy;

$R_3$ and $R_4$ are independently H, deuterium, halogen and $C_{1-4}$ alkyl, wherein the alkyl is optionally substituted with 1-3 groups selected from deuterium, F, Cl, Br and I;

ring A is phenyl,

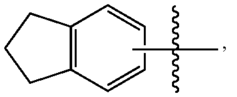

thienyl, thiazolyl, isothiazolyl, oxazolyl or isoxazolyl;

$R_7$ is H or $C_{1-3}$ alkyl, wherein the alkyl is optionally substituted with 1-3 groups selected from deuterium, halogen, $C_{1-4}$ alkoxy, deuterated $C_{1-4}$ alkoxy and halo $C_{1-4}$ alkoxy;

each $R_{10}$ is independently H, halogen, CN, $C_{1-4}$ alkyl, $C_{2-4}$ alkenyl, $C_{2-4}$ alkynyl, $C_{3-4}$ cycloalkyl or $C_{1-4}$ alkoxy, wherein the alkyl, alkenyl, alkynyl, cycloalkyl and alkoxy are optionally substituted with 1-3 groups selected from deuterium, halogen, $C_{1-4}$ alkyl and CN;

q is 1, 2 or 3;

the rest is as described in the second technical solution.

More specifically, the fourth technical solution of the present invention provides a compound represented by formula II, or a stereoisomer, solvate, or pharmaceutically acceptable salt thereof, wherein $R_1$, $R_2$, $R_a$ and $R_b$ are independently H, methoxy, ethoxy, propoxy, isopropoxy, $—O(CH_2)_m$ cyclopropyl, methyl, ethyl, propyl, isopropyl or $—(CH_2)_m$ cyclopropyl, wherein the methoxy, ethoxy, propoxy, isopropoxy, cyclopropyl, methyl, ethyl, propyl, isopropyl and cyclopropyl are optionally further substituted with 1-3 groups selected from deuterium, F, Cl, Br, I, methyl, ethyl, propyl, isopropyl, methoxy, ethoxy, propoxy, deuterated methyl, deuterated ethyl, deuterated propyl, deuterated methoxy, deuterated ethoxy, deuterated propoxy, halomethoxy, haloethoxy and halopropoxy;

optionally, $R_1$ and $R_2$ together with the atom to which they are attached form

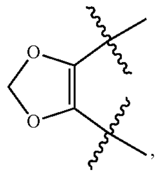 [SMILES: *C1=C(*)OCO1]

and are optionally substituted with 1-2 groups selected from deuterium, F, Cl, Br, I, methyl, ethyl, propyl, methoxy, ethoxy, propoxy, halomethyl, haloethyl and halopropyl;

$R_3$ and $R_4$ are independently H, deuterium, F, Cl, Br, I, methyl, ethyl or propyl, wherein the methyl, ethyl or propyl is optionally substituted with 1-3 groups selected from deuterium, F, Cl, Br and I;

ring A is phenyl,

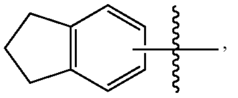

thienyl or thiazolyl;

$R_7$ is H, methyl, ethyl, propyl or isopropyl, wherein the methyl, ethyl, propyl or isopropyl is optionally substituted with 1-3 groups selected from deuterium, F, Cl, Br, I, methoxy, ethoxy, propoxy, deuterated methyl, deuterated ethyl, deuterated propyl, deuterated methoxy, deuterated ethoxy, deuterated propoxy, halomethoxy, haloethoxy and halopropoxy;

each $R_{10}$ is independently H, F, Cl, Br, I, CN, methyl, ethyl, propyl, isopropyl, n-butyl, isobutyl, ethenyl, propenyl, allyl, ethynyl, propynyl, cyclopropyl, cyclobutyl, methoxy, ethoxy or propoxy, wherein the methyl, ethyl, propyl, isopropyl, n-butyl, isobutyl, ethenyl, propenyl, allyl, ethynyl, propynyl, cyclopropyl, cyclobutyl, methoxy, ethoxy and propoxy are optionally substituted with 1-3 groups selected from deuterium, F, Cl, Br, I, methyl, ethyl, propyl and CN;

q is 2 or 3;

the rest is as described in the third technical solution.

More specifically, the fifth technical solution of the present invention provides a compound represented by formula I, or a stereoisomer, solvate, or pharmaceutically acceptable salt thereof, wherein the compound is selected from one of the following structures:

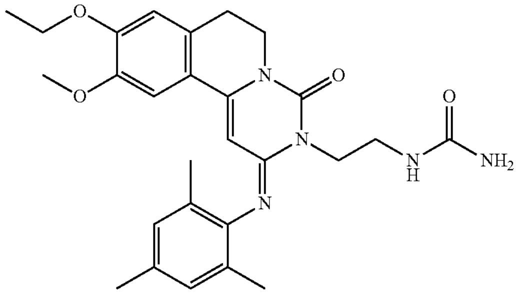

-continued
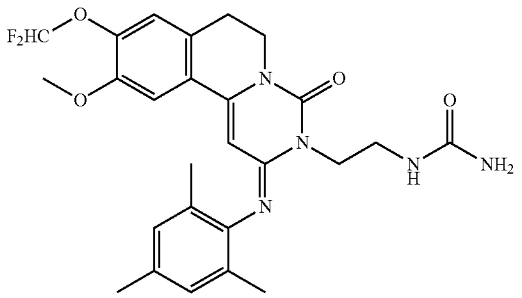
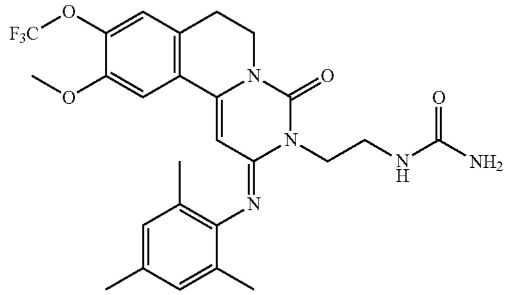
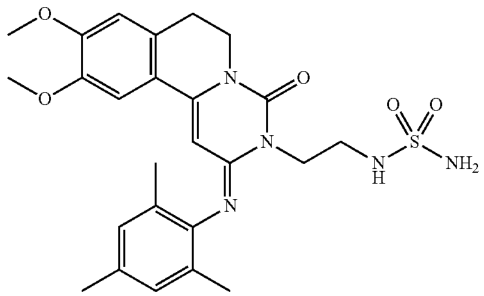
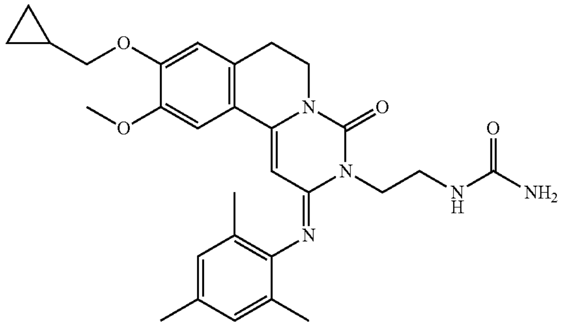
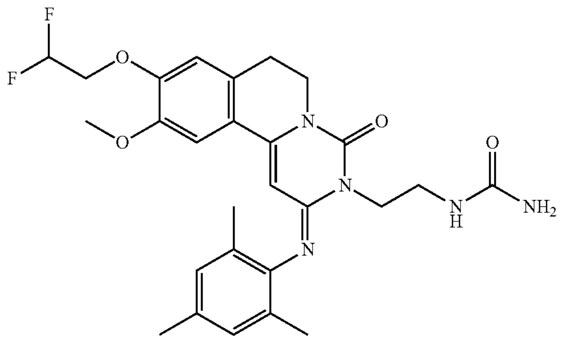
-continued
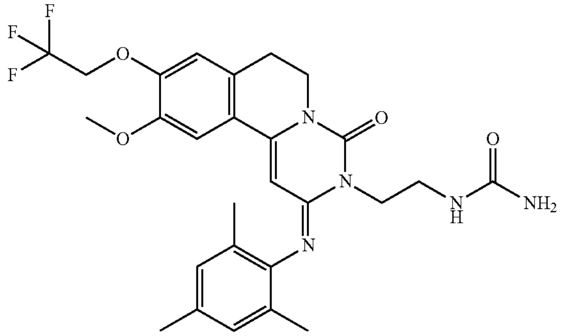
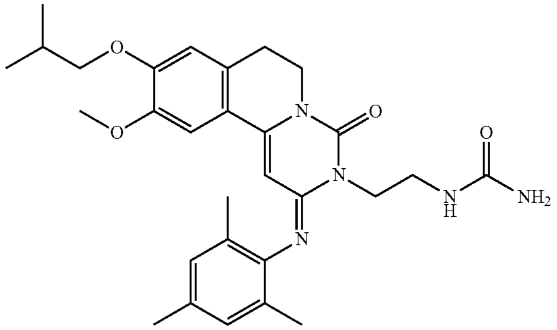
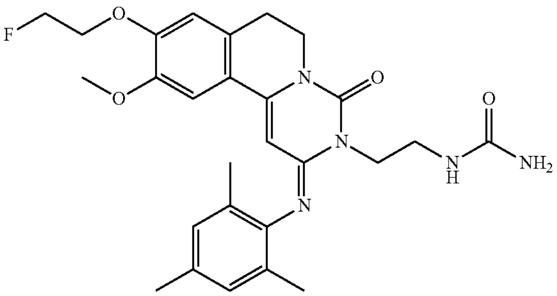
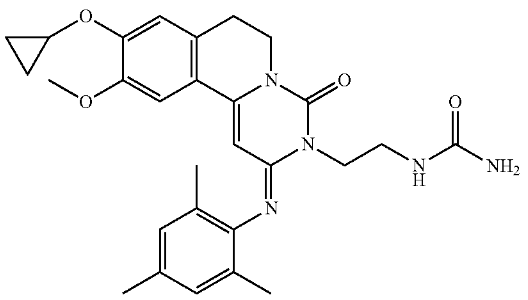
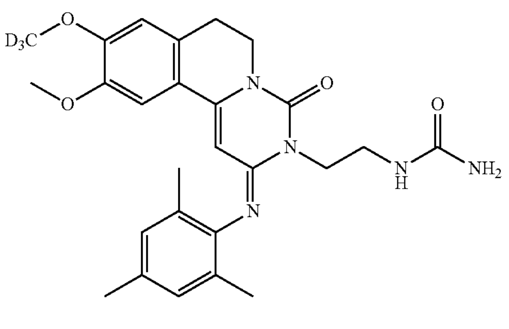

-continued
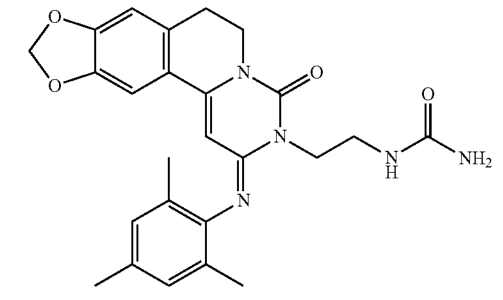
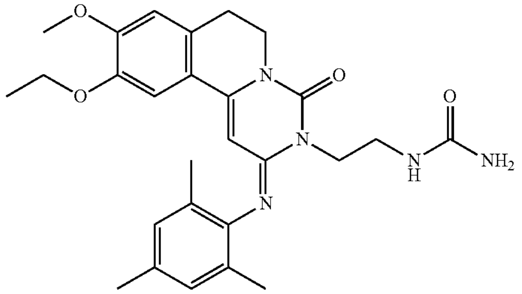
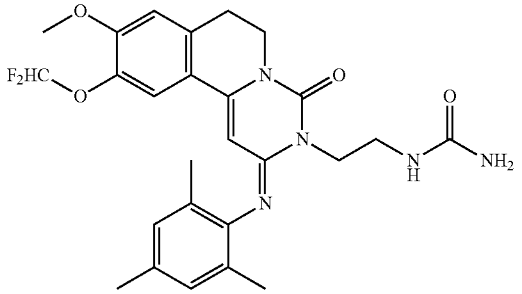
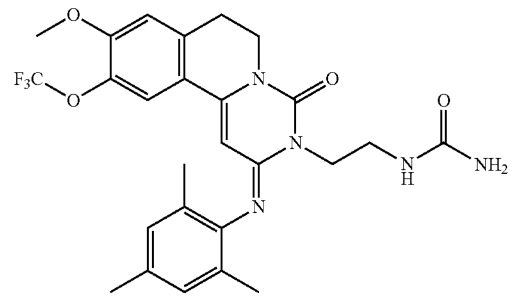
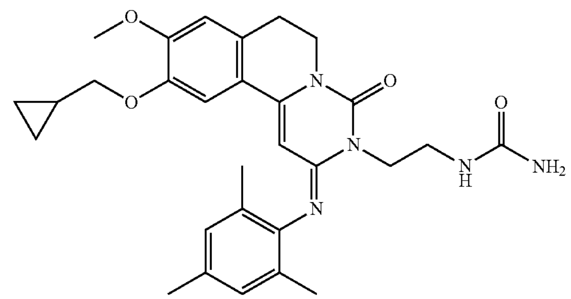
-continued
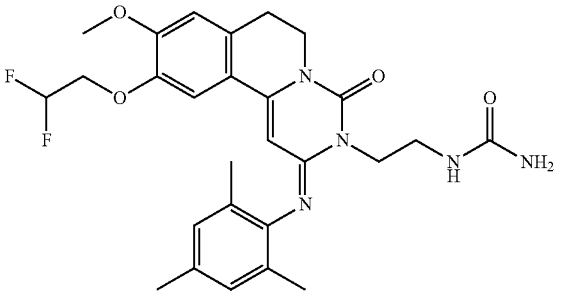
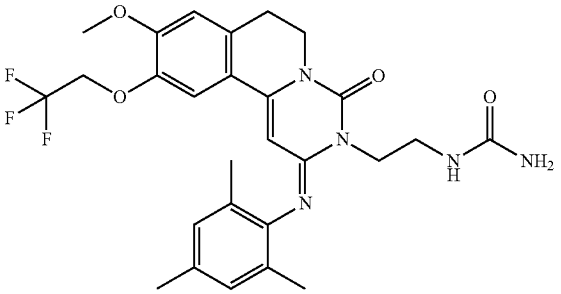
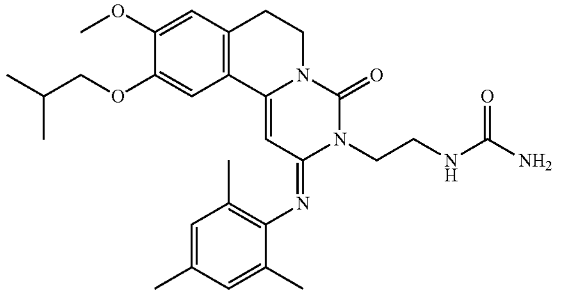
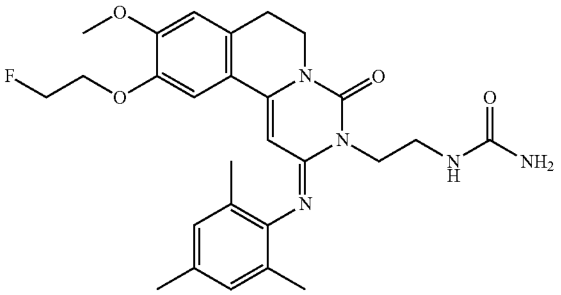
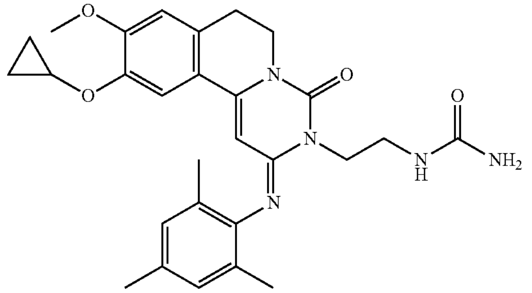

-continued
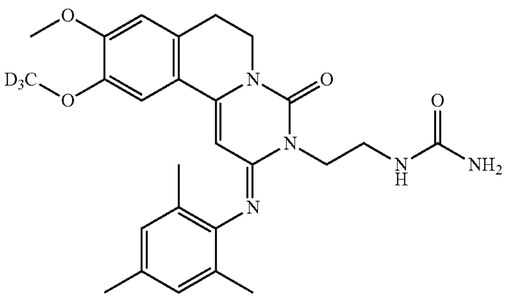
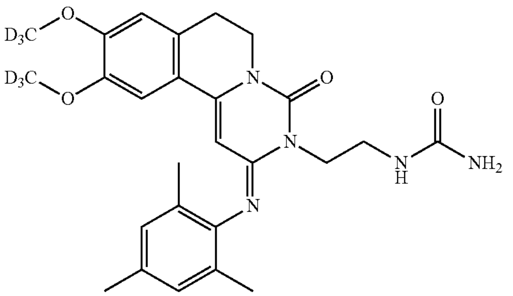
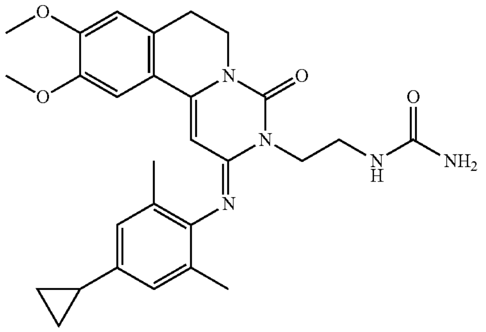
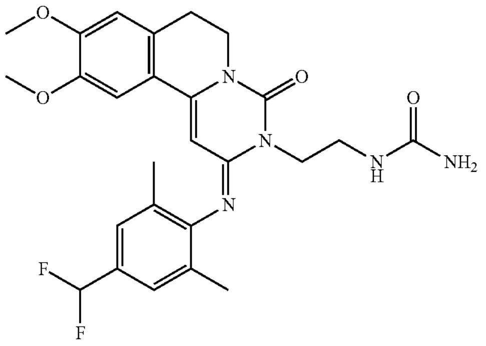
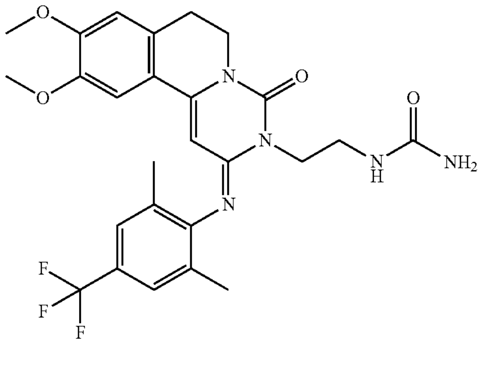
-continued
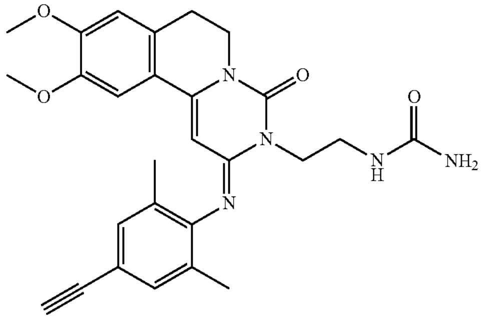
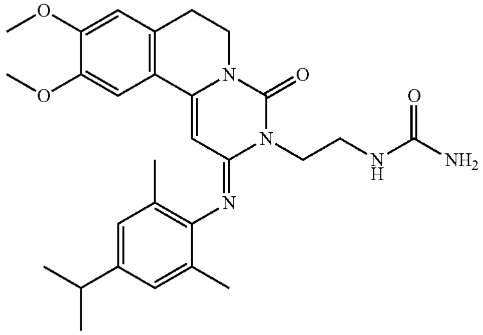
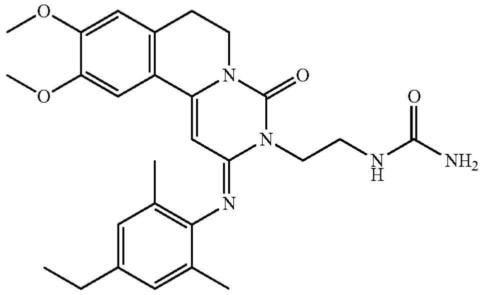
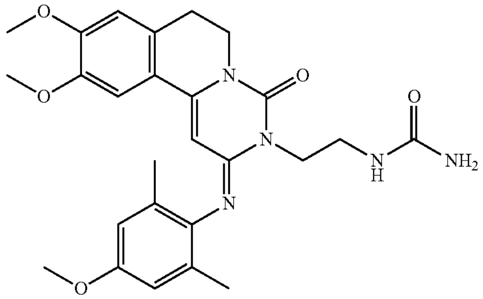
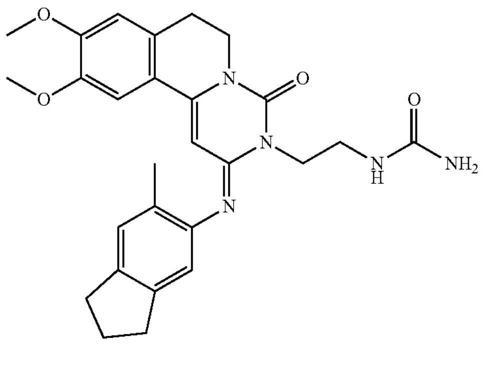

-continued

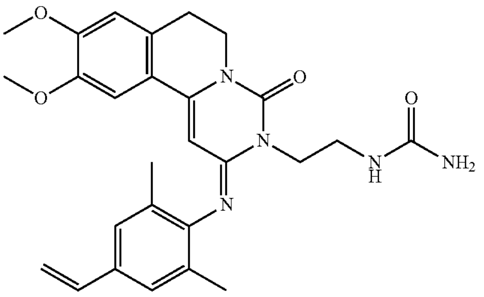

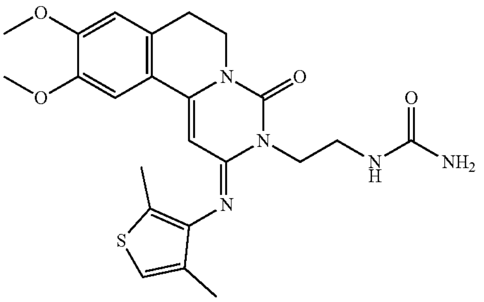

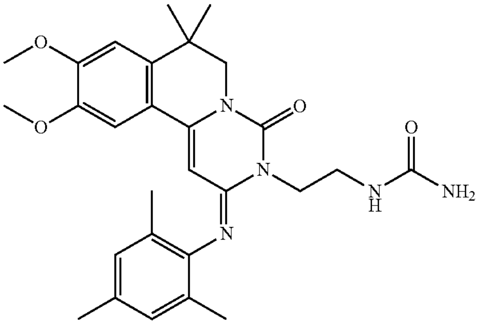

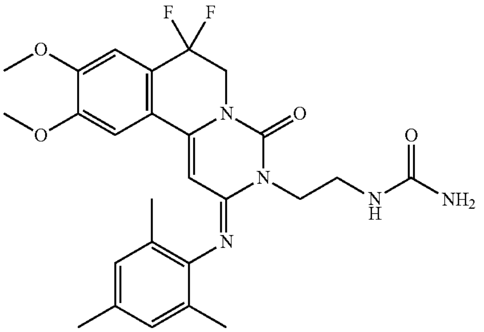

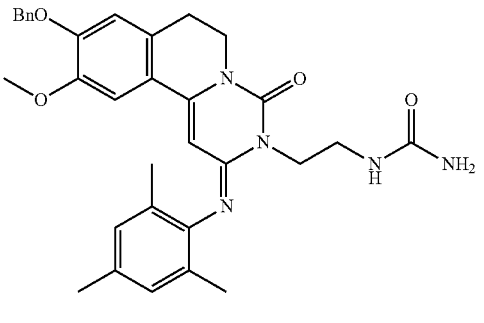

-continued

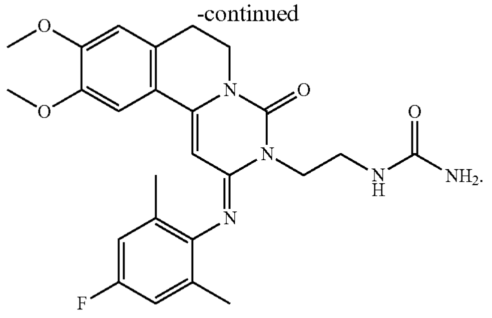

More specifically, the sixth technical solution of the present invention provides a pharmaceutical composition, comprising the compound, or the stereoisomer, solvate, or pharmaceutically acceptable salt thereof according to any one of the first to fifth technical solutions, and a pharmaceutically acceptable carrier and/or auxiliary agent.

More specifically, the seventh technical solution of the present invention provides the use of the compound, or the stereoisomer, solvate, or pharmaceutically acceptable salt thereof according to any one of the first to fifth technical solutions, or the composition according to the sixth technical solution in the preparation of a drug for the treatment/prevention of PDE3/4-mediated diseases.

Further, the PDE3/4-mediated diseases are selected from COPD and asthma.

Synthetic Route

Those skilled in the art would have been able to prepare the compounds of the present invention according to known organic synthesis techniques, and the starting materials used therein are commercially available chemicals and (or) compounds described in chemical documents. "Commercially available chemicals" are obtained from regular commercial sources, and suppliers include: Titan Technology Co., Ltd., Energy Chemical Co., Ltd., Shanghai Demo Co., Ltd., Chengdu Kelong Chemical Co., Ltd., Accela ChemBio Co., Ltd., PharmaBlock Sciences (Nanjing), Inc., WuXi Apptec Co., Ltd., J&K Scientific Co., Ltd., etc.

References and monographs in the art introduce in detail the synthesis of reactants that can be used to prepare the compounds described herein, or provide articles describing the preparation method for reference. The references and monographs include: "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992; Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000)

Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and similar reactants can be selectively identified by the indexes of known chemicals prepared by the Chemical Abstracts Service of the American Chemical Society, wherein the indexes are available in most public libraries and university libraries and online. Chemicals that are known but not commercially available in the catalog are optionally prepared by custom chemical synthesis plants, wherein many of standard chemical supply plants (such as those listed above) provide custom synthesis services. Reference document for the preparation and selection of the pharmaceutically acceptable salts of the compounds described herein is P. H. Stahl & C. G. Wermuth "Handbook of Pharmaceutical Salts", Verlag Helvetica Chimica Acta, Zurich, 2002.

Term

Unless otherwise specified, the terms of the present invention have the following meanings.

The carbon, hydrogen, oxygen, sulfur, nitrogen and halogen involved in the groups and compounds of the present invention all include isotopes thereof, and are optionally further replaced by one or more of the corresponding isotopes thereof, wherein the isotopes of carbon include $^{12}C$, $^{13}C$ and $^{14}C$; the isotopes of hydrogen include protium (H), deuterium (D, also known as heavy hydrogen) and tritium (T, also known as superheavy hydrogen); the isotopes of oxygen include $^{16}O$, $^{17}O$ and $^{18}O$; the isotopes of sulfur include $^{32}S$, $^{33}S$, $^{34}S$ and $^{36}S$; the isotopes of nitrogen include $^{14}N$ and $^{15}N$; the isotope of fluorine includes $^{19}F$; the isotopes of chlorine include $^{35}Cl$ and $^{37}Cl$; and the isotopes of bromine include $^{79}Br$ and $^{81}Br$.

The term "halogen" herein refers to F, Cl, Br, I, or isotopes thereof.

The term "halo" or "substituted with halogen" means that a group is substituted with one or more groups selected from F, Cl, Br, I, or isotopes thereof, wherein the upper limit of the number of halogen substituents is equal to the sum of the number of hydrogens that can be substituted in the group to be substituted. Without particular limitation, the number of halogen substituents is any integer between 1 and the upper limit, and when the number of halogen substituents is greater than 1, the group to be substituted can be substituted with the same or different halogen. Generally, the circumstances of being substituted with 1-5 halogen, 1-4 halogen, 1-3 halogen, 1-2 halogen, and 1 halogen are included.

The term "deuterium" refers to the isotope deuterium of hydrogen (H), which is synonymous with "D".

The term "deuterated" or "deuterated compound" refers to the case where a hydrogen atom on a group, such as alkyl, cycloalkyl, alkylene, aryl, heteroaryl, sulfydryl, heterocycloalkyl, alkenyl and alkynyl is substituted with at least one deuterium atom, wherein the upper limit of the number of deuterium substituents is equal to the sum of the number of hydrogens that can be substituted in the group to be substituted. Without particular limitation, the number of deuterium substituents is any integer between 1 and the upper limit, for example, 1-20 deuterium atoms, 1-10 deuterium atoms, 1-6 deuterium atoms, 1-3 deuterium atoms, 1-2 deuterium atoms or 1 deuterium atom.

Group "$C_{x-y}$" refers to a group comprising x to y carbon atoms, for example, "$C_{1-6}$ alkyl" refers to alkyl comprising 1-6 carbon atoms.

The term "alkyl" refers to a monovalent straight or branched saturated aliphatic hydrocarbon group, usually an alkyl group with 1 to 20 carbon atoms, or an alkyl group with 1 to 8 carbon atoms, or an alkyl group with 1 to 6 carbon atoms, or an alkyl group with 1 to 4 carbon atoms. Non-limiting examples of alkyl include methyl, ethyl, n-propyl, isopropyl, n-butyl, sec-butyl, neobutyl, tert-butyl, n-pentyl, isopentyl, neopentyl, n-hexyl, etc., and alkyl may be further substituted with a substituent.

The term "alkylene" refers to a divalent straight or branched saturated alkyl group. Examples of alkylene include, but are not limited to methylene, ethylidene, etc.

The term "haloalkyl" refers to an alkyl group in which one or more hydrogens are replaced by one or more halogen atoms (e.g., fluorine, chlorine, bromine, iodine, or isotopes thereof), wherein the upper limit of the number of halogen substituents is equal to the sum of the number of hydrogens that can be substituted in the alkyl group. Without particular limitation, the number of halogen substituents is any integer between 1 and the upper limit. Generally, the alkyl group is substituted with 1-5 halogen, 1-3 halogen, 1-2 halogen or 1 halogen; and when the number of halogen substituents is greater than 1, the alkyl group can be substituted with the same or different halogen. Specific examples include, but are not limited to $—CF_3$, $—CH_2Cl$, $—CH_2CF_3$, $—CCl_2$, $CF_3$, etc.

The term "alkoxy" or "alkyloxy" refers to —O-alkyl, such as —O—$C_{1-8}$ alkyl, —O—$C_{1-6}$ alkyl, —O—$C_{1-4}$ alkyl or —O—$C_{1-2}$ alkyl. Non-limiting and specific examples of alkoxy or alkyloxy include methoxy, ethoxy, n-propoxy, isopropoxy, n-butoxy, sec-butoxy, tert-butoxy, n-pentoxy, n-hexyloxy, cyclopropoxy, cyclobutoxy, etc. The alkoxy may be optionally substituted with a substituent.

The term "haloalkoxy" refers to —O-haloalkyl, such as —O-halo $C_{1-8}$ alkyl, —O-halo $C_{1-6}$ alkyl, —O-halo $C_{1-4}$ alkyl or —O-halo $C_{1-2}$ alkyl; the upper limit of the number of halogen substituents is equal to the sum of the number of hydrogens that can be substituted in the group to be substituted. Without particular limitation, the number of halogen substituents is any integer between 1 and the upper limit, preferably 1-5 halogen, 1-3 halogen, 1-2 halogen, and 1 halogen; and when the number of halogen substituents is greater than 1, the group to be substituted can be substituted with the same or different halogen. Non-limiting examples of haloalkoxy include monofluoromethoxy, difluoromethoxy, trifluoromethoxy, difluoroethyloxy, etc.

The term "alkenyl" refers to a straight or branched hydrocarbon group comprising at least one carbon-carbon double bond (C═C) and generally comprises 2 to 18 carbon atoms, such as 2 to 8 carbon atoms, further such as 2 to 6 carbon atoms, and still further such as 2 to 4 carbon atoms. Examples of alkenyl include, but are not limited to ethenyl, allyl, 1-propenyl, 2-propenyl, 1-butenyl, 2-butenyl, 3-butenyl, 1-pentenyl, 2-pentenyl, 3-pentenyl, 4-pentenyl, 1-methyl-1-butenyl, 2-methyl-1-butenyl, 2-methyl-3-butenyl, 1-hexenyl, 2-hexenyl, 3-hexenyl, 4-hexenyl, 5-hexenyl, 1-methyl-1-pentenyl, 2-methyl-1-pentenyl, 1-heptenyl, 2-heptenyl, 3-heptenyl, 4-heptenyl, 1-octenyl, 3-octenyl, 1-nonenyl, 3-nonenyl, 1-decenyl, 4-decenyl, 1,3-butadiene, 1,3-pentadiene, 1,4-pentadiene, 1,4-hexadiene, etc.; and the alkenyl may further be optionally substituted with a substituent.

The term "alkenylene" refers to a straight or branched divalent unsaturated hydrocarbon group comprising at least one carbon-carbon double bond (C═C). Unless otherwise specified, the alkenylene contains 2-6 carbon atoms, preferably 2-4 carbon atoms. Non-limiting examples of alkenylene include ethenylene, and the alkenylene may be optionally substituted with a substituent.

The term "alkynyl" refers to a straight or branched hydrocarbon group comprising at least one carbon-carbon triple bond (C═C) and generally comprises 2 to 18 carbon atoms, further comprises 2 to 8 carbon atoms, further comprises 2 to 6 carbon atoms, and still further comprises 2 to 4 carbon atoms. Examples of alkynyl include, but are not limited to ethynyl, 1-propynyl, 2-propynyl, butynyl, 2-butynyl, 3-butynyl, 1-methyl-2-propynyl, 4-pentynyl, 3-pentynyl, 1-methyl-2-butynyl, 2-hexynyl, 3-hexynyl, 2-heptynyl, 3-heptynyl, 4-heptynyl, 3-octynyl, 3-nonynyl, 4-decynyl, etc.; and the alkynyl may be optionally substituted with a substituent.

The term "alkynylene" refers to a straight or branched divalent unsaturated hydrocarbon group comprising a carbon-carbon triple bond (C≡C) and generally comprises 2-6 carbon atoms, and further comprises 2-4 carbon atoms. Non-limiting examples of alkynylene include ethynylene, propynylene and butynylene; and the alkynylene may be optionally substituted with a substituent.

The term "cycloalkyl" refers to a saturated or partially unsaturated, non-aromatic carbocyclic hydrocarbon group containing no ring heteroatoms. The cycloalkyl may be monocyclic, bicyclic or polycyclic, the bicyclic or polycyclic cycloalkyl may be in the form of a fused ring, a spiro ring, a bridged ring or a combination thereof, and may comprise one or more aromatic rings, but the ring system is non-aromatic as a whole, and the attachment site may be on an aromatic ring or a non-aromatic ring. Generally, the cycloalkyl contains 3 to 20 carbon atoms, further contains 3-8 carbon atoms, and still further contains 3-6 carbon atoms; when the cycloalkyl is monocyclic cycloalkyl, the cycloalkyl contains 3-15 carbon atoms, or 3-10 carbon atoms, or 3-8 carbon atoms, or 3-6 carbon atoms; when the cycloalkyl is bicyclic or polycyclic cycloalkyl, the cycloalkyl contains 5-12 carbon atoms, or 5-11 carbon atoms, or 6-10 carbon atoms. Non-limiting examples of cycloalkyl include cyclopropyl, cyclobutyl, cyclopentyl, cyclohexyl, cycloheptyl, butenyl, cyclopentenyl, cyclohexenyl,

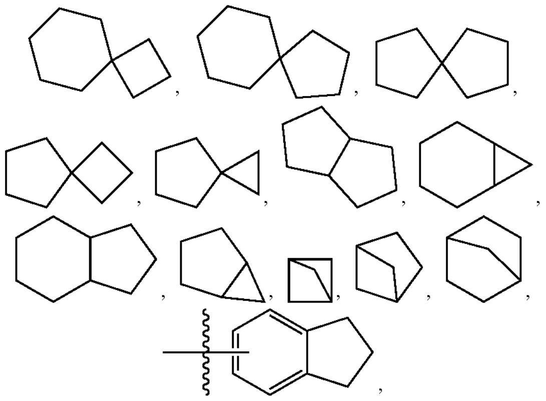

etc., and the cycloalkyl may be optionally substituted with a substituent.

The term "cycloalkylene" refers to a divalent group of cycloalkyl.

The term "aryl" refers to an aromatic carbocycle that does not contain heteroatoms, including monocyclic aryl and fused aryl. Generally, the aryl contains 6 to 13 carbon atoms, and further contains 6 to 9 carbon atoms, and it is further phenyl. Non-limiting examples of aryl include phenyl, naphthyl, anthryl and phenanthryl, and the aryl may be optionally substituted with a substituent.

"Carbocycle" or "carbocyclyl" refers to a saturated, partially unsaturated, or aromatic carbocycle, and its meaning includes aryl and cycloalkyl. The carbocycle may be monocyclic, bicyclic or polycyclic, and the bicyclic or polycyclic carbocycle may be in the form of a bridged ring, a fused ring, a spiro ring and a combination thereof. Generally, the carbocycle contains 3-12 carbon atoms, or 3-10 carbon atoms, or 3-6 carbon atoms. Non-limiting examples of the monocyclic carbocycle include cyclopropyl, cyclobutyl, cyclopentyl, cyclohexyl, cycloheptyl, phenyl, etc. A bicyclic bridged ring includes

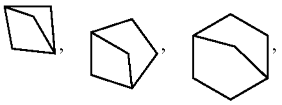

etc., a bicyclic fused ring includes

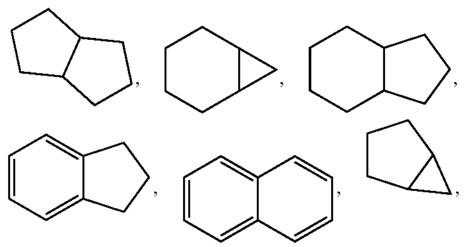

etc., and a bicyclic spiro ring includes

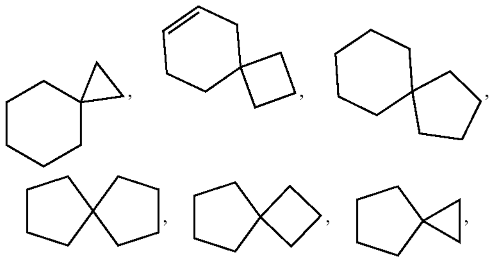

etc. The carbocycle may be optionally substituted with a substituent.

"Heterocycloalkyl" refers to a saturated or partially unsaturated non-aromatic carbocycle containing 1, 2, 3, or 4 heteroatoms selected from N, S or O. The heterocycloalkyl may be monocyclic, bicyclic or polycyclic, the bicyclic or polycyclic heterocycloalkyl may be in the form of a bridged ring, a fused ring, a spiro ring or a combination thereof, and may comprise one or more aromatic rings or heteroaromatic rings, but the ring system is non-aromatic as a whole, and the attachment site may be on an aromatic ring or a non-aromatic ring. Generally, the heterocycloalkyl is a 3- to 20-membered ring. When the heterocycloalkyl is monocyclic heterocycloalkyl, the heterocycloalkyl is usually a 3- to 15-membered ring, or a 3- to 10-membered ring, or a 3- to 8-membered ring, or a 3- to 6-membered ring; when the heterocycloalkyl is bicyclic or polycyclic heterocycloalkyl, the heterocycloalkyl is usually a 5- to 12-membered ring, or a 5- to 11-membered ring, or a 6- to 9-membered ring. The heteroatoms N and S include their oxidation states. Non-limiting examples of heterocycloalkyl include azetidinyl, morpholinyl, piperazinyl, piperidyl, tetrahydropyranyl, oxetanyl, pyranyl, azacyclopentenyl, azacyclohexenyl, oxacyclopentenyl, oxacyclohexenyl, etc., and the heterocycloalkyl may be optionally substituted with a substituent.

"Heteroaromatic ring" or "heteroaryl", unless otherwise specified, refers to an aromatic ring containing 1 to 4 heteroatoms selected from N, O or S and their oxidation states, which may be monocyclic, bicyclic or polycyclic, wherein the bicyclic or polycyclic heteroaromatic ring or heteroaryl may be in the form of a bridged ring, a fused ring, a spiro ring and a combination thereof. The bicyclic or polycyclic heteroaromatic ring or heteroaryl can be formed by fusion of heteroaryl to aryl, or of heteroaryl to heteroaryl, wherein the heteroaryl or aryl may be the attachment site. Non-limiting examples of heteroaromatic ring or heteroaryl include furyl, thienyl, pyrrolyl, oxazolyl, thiazolyl, imidazolyl, pyrazolyl, pyridyl, pyrimidyl, pyridazinyl, pyrazinyl, indolyl, purinyl,

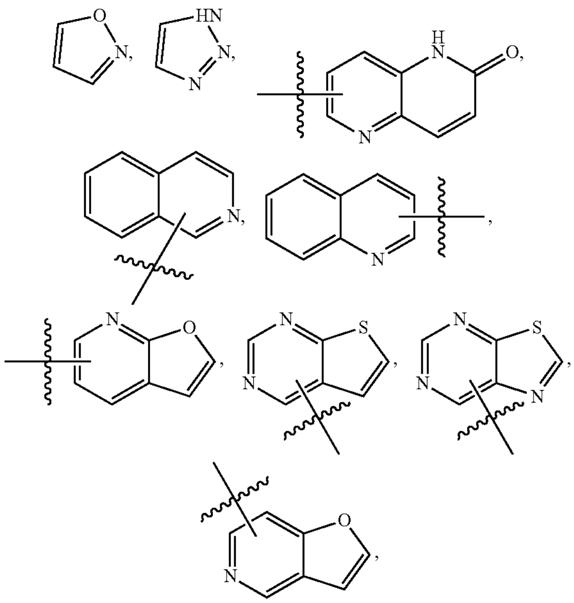

etc. The heteroaryl may be optionally substituted with a substituent.

The term "heterocycle" or "heterocyclyl" refers to a saturated or unsaturated, aromatic or non-aromatic ring containing 1 to 4 heteroatoms selected from N, O or S and their oxidation states, and its meaning includes heteroaryl and heterocycloalkyl. The heterocycle may be in the form of a monocyclic heterocycle, a bicyclic bridged heterocycle, a bicyclic fused heterocycle, a bicyclic spiro heterocycle or a combination thereof. The heterocycle is usually a 3- to 12-membered heterocycle, or a 5- to 12-membered heterocycle, or a 5- to 7-membered heterocycle. Heterocyclyl can be connected to a heteroatom or a carbon atom. Non-limiting examples of heterocyclyl include oxiranyl, aziridinyl, oxetanyl, azetidinyl, 1,3-dioxolanyl, 1,4-dioxolanyl, 1,3-dioxanyl, piperazinyl, azepanyl, pyridyl, furyl, thienyl, pyranyl, N-alkylpyrrolyl, pyrimidyl, pyrazinyl, pyrazolyl, pyridazinyl, imidazolyl, piperidyl, morpholinyl, thiomorpholinyl, 1,3-dithianyl, dihydrofuryl, dihydropyranyl, dithiolanyl, tetrahydrofuryl, tetrahydropyrrolyl, tetrahydroimidazolyl, oxazolyl, dihydrooxazolyl, tetrahydrooxazolyl, tetrahydrothiazolyl, tetrahydropyranyl, benzoimidazolyl, benzopyridyl, pyrrolopyridyl, benzodihydrofuryl, azabicyclo[3.2.1]octanyl, azabicyclo[5.2.0]nonanyl, oxatricyclo[5.3.1.1]dodecyl, azaadamantyl, oxaspiro[3.3]heptanyl,

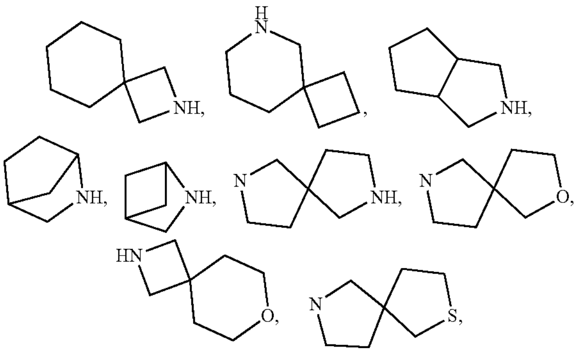

etc., and the heterocycle may be optionally substituted with a substituent.

The term "heterocyclene" refers to a substituted or unsubstituted, saturated or unsaturated, aromatic or non-aromatic, divalent heterocyclyl group. Non-limiting examples of heterocyclene include

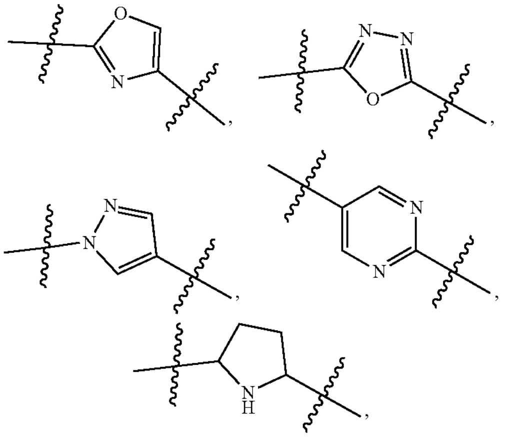

etc.

The term "spiro ring" refers to a polycyclic group sharing one carbon atom (referred to as a spiro atom) between rings, which may contain 0 or at least 1 double or triple bond, and may contain 0 to 5 heteroatoms selected from N, O, S, P, Si and their oxidation states. Generally, a spiro ring is a 6- to 14-membered ring, or a 6- to 12-membered ring, or a 6- to 10-membered ring. Generally, a spiro ring is a spiro ring formed by a three-membered ring and a three-membered ring, a three-membered ring and a four-membered ring, a three-membered ring and a five-membered ring, a three-membered ring and a six-membered ring, a four-membered ring and a four-membered ring, a four-membered ring and a five-membered ring, a four-membered ring and a six-membered ring, a five-membered ring and a five-membered ring or a five-membered ring and a six-membered ring. Non-limiting examples of the spiro ring include:

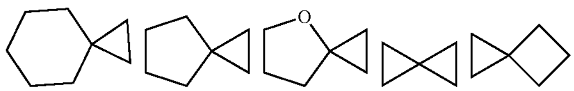
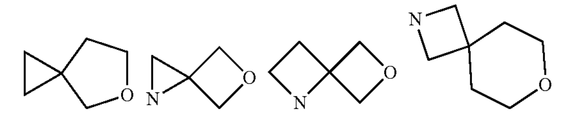
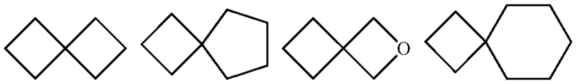
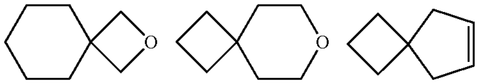
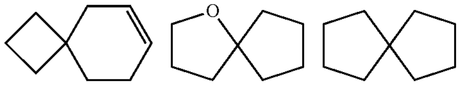
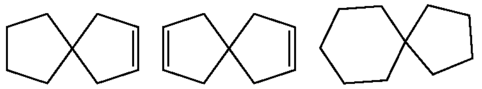
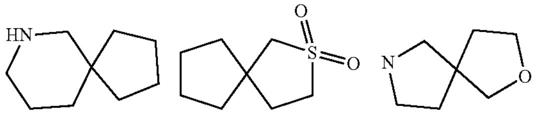
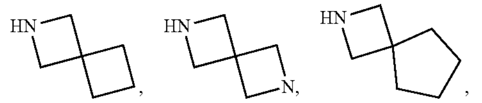
, , ,
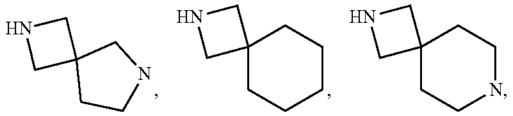
, , ,
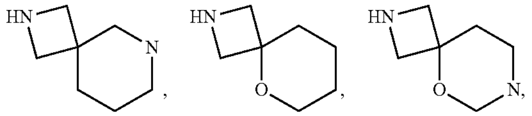
, , ,
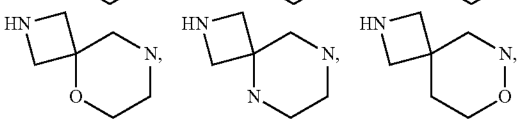
, , ,
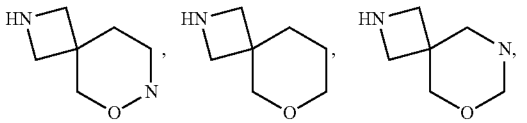
, , ,
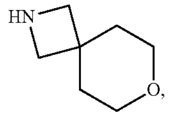
, and the spiro ring may be optionally substituted with a substituent.

The term "fused ring" refers to a polycyclic group in which the rings share two adjacent ring atoms and one chemical bond, which may contain one or more double or triple bonds, and may contain 0 to 5 heteroatoms selected from N, S, O, P, Si and their oxidation states. Generally, a fused ring is a 5- to 20-membered ring, or a 5- to 14-membered ring, or a 5- to 12-membered ring or a 5- to 10-membered ring. Generally, a fused ring is in the form of a three-membered ring fused a four-membered ring (indicating a fused ring formed by a three-membered ring and a four-membered ring, and either the three-membered ring or the four-membered ring may be possibly used as the basic ring according to the IUPC nomenclature; similarly hereinafter), a three-membered ring fused a five-membered ring, a three-membered ring fused a six-membered ring, a four-membered ring fused a four-membered ring, a four-membered ring fused a five-membered ring, a four-membered ring fused a six-membered ring, a five-membered ring fused a five-membered ring, a five-membered ring fused a six-membered ring, and a six-membered ring fused a six-membered ring. Non-limiting examples of the fused ring include purine, quinoline, isoquinoline, benzopyran, benzofuran, benzothiophene,

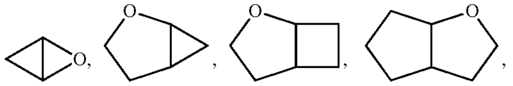
, , , ,
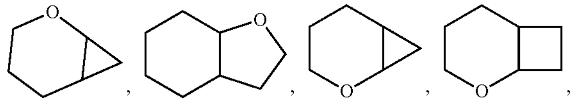
, , , ,
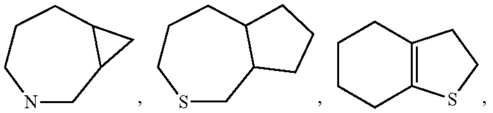
, , ,
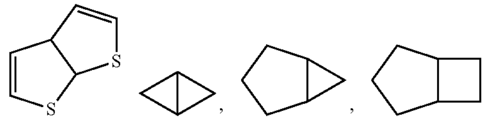
, , ,
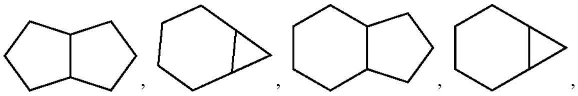
, , , ,
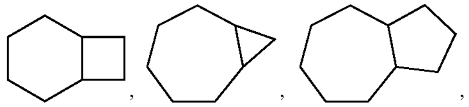
, , ,
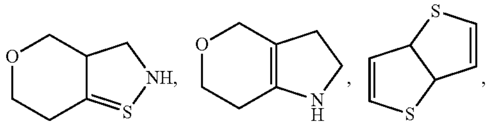
, , ,
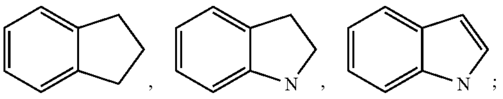
, , ;

and the fused ring may be optionally substituted with a substituent.

The term "bridged ring" refers to a ring system in which two non-adjacent ring atoms are shared between two rings, which may contain one or more double or triple bonds. The bridged ring may contain 0 to 5 heteroatoms selected from N, S, O, P, Si and their oxidation states. Generally, the bridged ring has 5 to 20, or 5 to 14, or 5 to 12, or 5 to 10 ring atoms. Non-limiting examples of the bridged ring include adamantane,

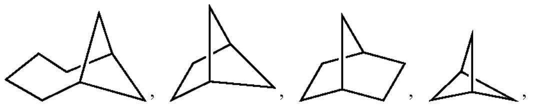,

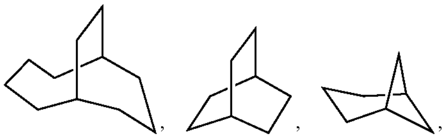,

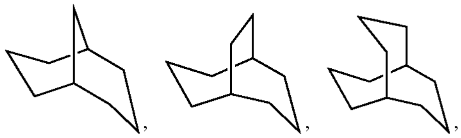,

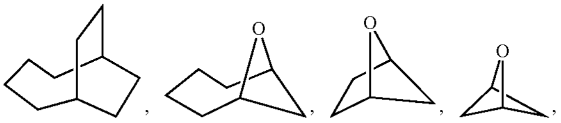,

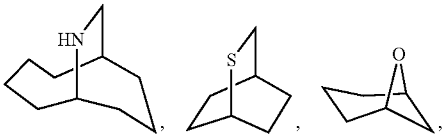,

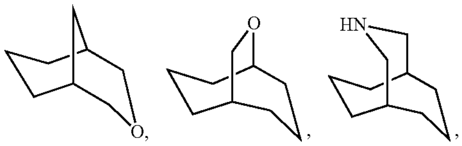,

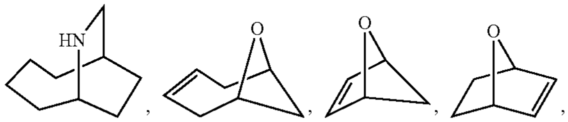,

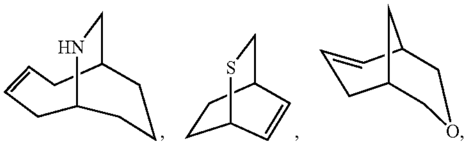,

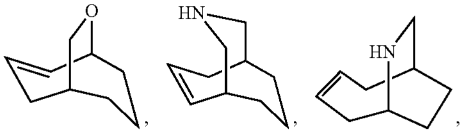,

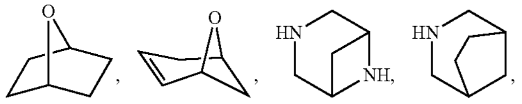,

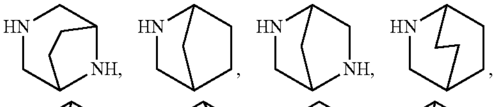,

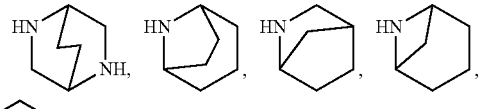,

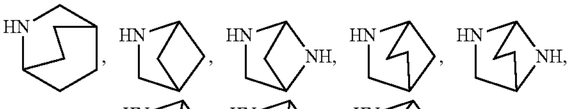,

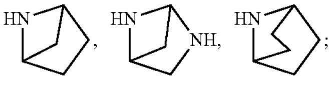;

and the bridged ring may be optionally substituted with a substituent.

Unless otherwise specified, the term "substitution" or "substituent" refers to any substitution at a position allowed by chemical theory, and the number of substituents conforms to the rules of chemical bonding. Exemplary substituents include, but are not limited to: $C_{1-6}$ alkyl, $C_{2-6}$ alkenyl, $C_{2-6}$ alkynyl, $C_{3-8}$ heteroalkyl, $C_{5-12}$ aryl, 5- to 12-membered heteroaryl, hydroxyl, $C_{1-6}$ alkoxy, $C_{5-12}$ aryloxy, thiol, $C_{1-6}$ alkylthio, cyano, halogen, $C_{1-6}$ alkylthiocarbonyl, $C_{1-6}$ alkylcarbamoyl, N-carbamoyl, nitro, silyl, sulfinyl, sulfonyl, sulfoxide, halo $C_{1-6}$ alkyl, halo $C_{1-6}$ alkoxy, amino, phosphonic acid, —$CO_2$($C_{1-6}$ alkyl), —OC(═O)($C_{1-6}$ alkyl), —$OCO_2$($C_{1-6}$ alkyl), —C(═O)$NH_2$, —C(═O)N($C_{1-6}$ alkyl)$_2$, —OC(═O)NH($C_{1-6}$ alkyl), —NHC(═O)($C_{1-6}$ alkyl), —N($C_{1-6}$ alkyl)C(═O)($C_{1-6}$ alkyl), —$NHCO_2$($C_{1-6}$ alkyl), —NHC(═O)N($C_{1-6}$ alkyl)$_2$, —HC(═O)NH($C_{1-6}$ alkyl), —NHC(═O)$NH_2$, —$NHSO_2$($C_{1-6}$ alkyl), —$SO_2$N($C_{1-6}$ alkyl)$_2$, —$SO_2$NH($C_{1-6}$ alkyl), —$SO_2NH_2$, —$SO_2C_{1-6}$ alkyl, etc.

The term "optional" or "optionally" means that the events or circumstances subsequently described may but not necessarily occur, and the description includes the occasions where the events or circumstances occur or do not occur. For example, "alkyl optionally substituted with F" means that the alkyl may but not necessarily be substituted with F, and the description includes the case where the alkyl is substituted with F and the case where the alkyl is not substituted with F.

The term "pharmaceutically acceptable salt" refers to a salt of the compound of the present invention, which salt maintains the biological effectiveness and characteristics of a free acid or a free base and is obtained by reacting the free acid with a non-toxic inorganic base or organic base, or reacting the free base with a non-toxic inorganic acid or organic acid.

The term "pharmaceutical composition" represents a mixture of one or more compounds described herein or the stereoisomers, solvates, pharmaceutically acceptable salts or co-crystals thereof and other components comprising physiologically/pharmaceutically acceptable carriers and/or excipients.

The term "carrier" refers to: a system that does not cause significant irritation to the organism and does not eliminate the biological activity and characteristics of the administered compound, and can change the way the drug enters the human body and the distribution of the drug in the body, control the release rate of the drug and delivery the drug to targeted organs. Non-limiting examples of the carrier include microcapsule, microsphere, nanoparticle, liposome, etc.

The term "excipient" refers to: a substance that is not a therapeutic agent per se, but used as a diluent, auxiliary agent, adhesive and/or vehicle for addition to a pharmaceutical composition, thereby improving the disposal or storage properties thereof, or allowing to or promoting the formation of a compound or a pharmaceutical composition into a unit dosage form for administration. As is known to those skilled in the art, a pharmaceutically acceptable excipient can provide various functions and can be described as a wetting agent, a buffer, a suspending agent, a lubricant, an emulsifier, a disintegrating agent, an absorbent, a preservative, a surfactant, a colorant, a flavoring agent and a sweetening agent. Examples of the pharmaceutically acceptable excipient include, but are not limited to: (1) sugars, such as lactose, glucose and sucrose; (2) starch, such as corn starch and potato starch; (3) cellulose and its derivatives, such as sodium carboxymethyl cellulose, ethyl cellulose, cellulose acetate, hydroxypropyl methylcellulose, hydroxypropyl cellulose, microcrystalline cellulose and croscarmellose (such as croscarmellose sodium); (4) tragacanth powder; (5) malt; (6) gelatin; (7) talc; (8) excipients, such as cocoa butter or suppository wax; (9) oils, such as peanut oil, cottonseed oil, safflower oil, sesame oil, olive oil, corn oil and soybean oil; (10) diols, such as propylene glycol; (11) polyols, such as glycerin, sorbitol, mannitol and polyethylene glycol; (12) esters, such as ethyl oleate and ethyl laurate; (13) agar; (14) buffers, such as magnesium hydroxide and aluminum hydroxide; (15) alginic acid; (16) pyrogen-free water; (17) isotonic saline; (18) Ringer's solution; (19) ethanol; (20) pH buffered solution; (21) polyester, polycarbonate and/or polyanhydride; and (22) other non-toxic compatible substances used in a pharmaceutical preparation.

The term "stereoisomer" refers to an isomer produced as a result of different spatial arrangement of atoms in molecules, including cis-trans isomers, enantiomers and conformational isomers.

The compounds of the present invention also include tautomers thereof, for example, when the present invention describes the left side compound in which the pyrimidine ring is substituted with OH, the right side tautomer compound is also included.

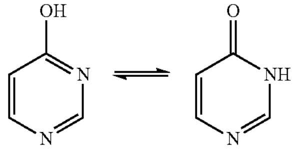 [SMILES: Oc1ccncn1 ; O=c1ccnc[nH]1]

The term "solvate" refers to a substance formed by the compound of the present invention or the salt thereof and a stoichiometric or non-stoichiometric solvent bound by intermolecular non-covalent forces. When the solvent is water, the solvate is a hydrate.

The term "co-crystal" refers to a crystal formed by the combination of active pharmaceutical ingredient (API) and co-crystal former (CCF) under the action of hydrogen bonds or other non-covalent bonds. The pure state of API and CCF are both solid at room temperature, and there is a fixed stoichiometric ratio among various components. The co-crystal is a multi-component crystal, which includes both a binary co-crystal formed between two neutral solids and a multi-element co-crystal formed between a neutral solid and a salt or solvate.

DETAILED DESCRIPTION OF EMBODIMENTS

The content of the present invention is described in detail with the following examples. If a specific condition is not indicated in the examples, a conventional condition is used in an experimental method. The listed examples are intended to better illustrate the content of the present invention, but should not be construed as limiting the content of the present invention. According to the above-mentioned content of the invention, those skilled in the art can make unsubstantial modifications and adjustments to the examples, which still fall within the protection scope of the present invention.

Example 1

(E)-1-(2-(2-(mesitylimino)-10-methoxy-9-(methoxy-d3)-4-oxo-6,7-dihydro-2H-pyrimido[6,1-a]isoquinolin-3(4H)-yl)ethyl)urea (Compound 1)

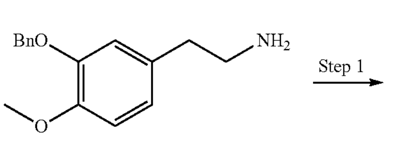

1A

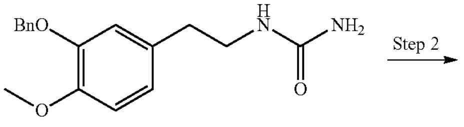

1B

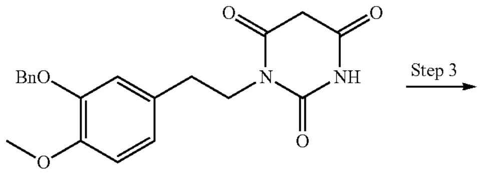

1C

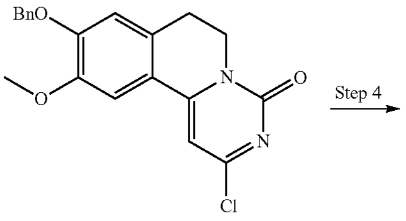

1D

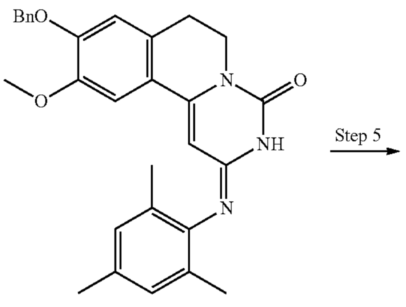

1E

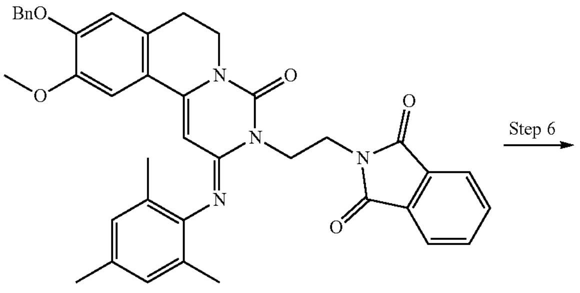

1F

-continued

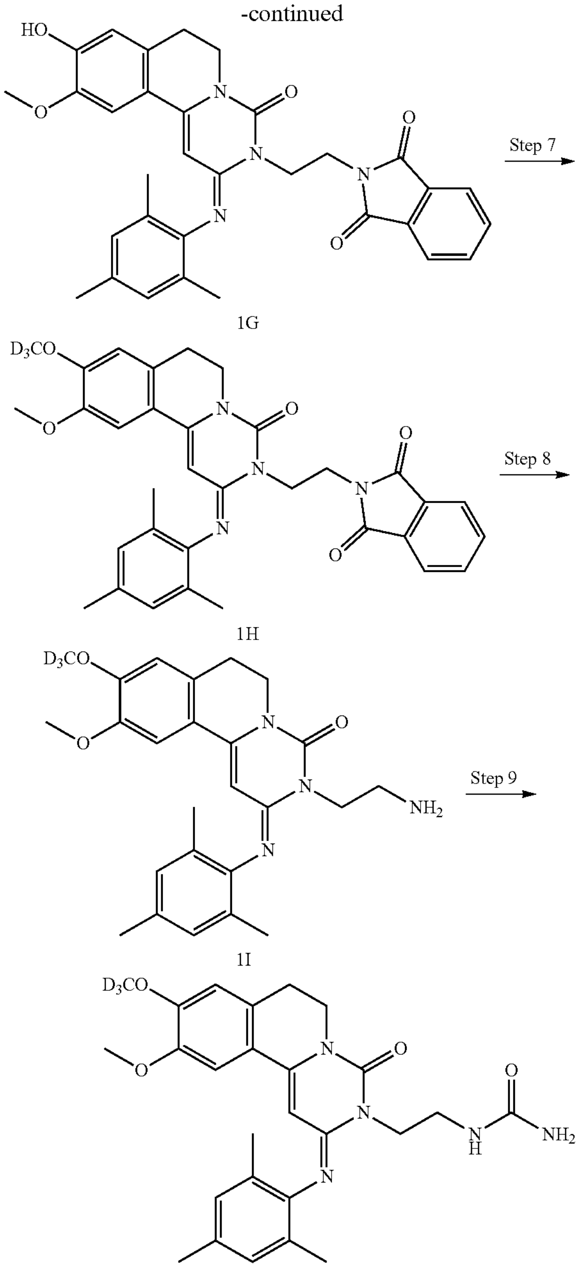

1G

1H

1I

Compound 1

Step 1

Compound 2-(3-(benzyloxy)-4-methoxyphenyl)ethan-1-amine (1A) (synthesized with reference to the method described in *J. Med. Chem.* 2013, 56, 23, 9673-9682) (51.5 g, 0.20 mol) was dissolved in water (300 mL), potassium cyanate (32.4 g, 0.40 mol) was added portionwise, the mixture was uniformly stirred, and then 2N hydrochloric acid (240 mL) was added dropwise. After the dropwise addition was completed, the mixture was refluxed and reacted overnight. The reaction liquid was cooled to 0° C. and filtered, and the filter cake was rinsed with ice ethanol and dried, to afford target compound 1B (38.0 g, yield: 63%).

LC-MS (ESI): m/z=301.2 $[M+H]^+$.

Step 2

Compound 1B (38 g, 0.13 mol) was dissolved in anhydrous ethanol (300 mL), diethyl malonate (27 g, 0.17 mol) was added, the system was uniformly stirred, and then sodium ethoxide (133 g, 0.39 mol, 20 wt % in EtOH) was added dropwise. After the dropwise addition was completed, the mixture was refluxed and reacted overnight. The system was concentrated to 150 mL under reduced pressure, diluted with water (150 mL), adjusted to pH 6.0 with 5N hydrochloric acid and filtered, and the filter cake was washed with water (150 mL) and dried, to afford target compound 1C (42 g, yield: 65.9%).

LC-MS (ESI): m/z=369.1 $[M+H]^+$

Step 3

Compound 1C (42 g, 114 mmol) was dissolved in phosphorus oxychloride (300 mL), and the mixture was reacted overnight at 120° C. The reaction liquid was cooled to room temperature and then concentrated under reduced pressure, the resulting residue was slowly added to ice water (300 mL), and saturated sodium bicarbonate aqueous solution was added portionwise to adjust to pH=6.0. The mixture was extracted with dichloromethane (500 mL×3), the organic phases were combined, dried over anhydrous sodium sulfate, filtered and concentrated, and the residue was separated by silica gel column chromatography (DCM:MeOH (v/v) =40:1), to afford the target compound (12.7 g, yield: 30%).

LC-MS (ESI): m/z=369.1 $[M+H]^+$.

$^1H$ NMR (400 MHz, $CDCl_3$) δ 7.48-7.32 (m, 5H), 7.14 (s,1H), 6.80 (s, 1H), 6.64 (s, 1H), 5.23 (s, 2H), 4.20 (t, 2H), 3.96 (s, 3H), 2.94 (t, 2H).

Step 4

1D (8.2 g, 22.2 mmol) was dissolved in isopropanol (120 mL), 2,4,6-trimethylaniline (4.46 g, 33 mmol) was added, and after the addition was completed, the mixture was reacted at 90° C. for 24 hours. The reaction liquid was cooled to room temperature and concentrated under reduced pressure, saturated sodium bicarbonate aqueous solution (100 mL) was added to the residue, and the mixture was extracted with dichloromethane (100 mL×3). The organic phases were combined, washed with saturated sodium chloride aqueous solution (100 mL), dried over anhydrous sodium sulfate and filtered, the filtrate was concentrated under reduced pressure, and the residue was separated by silica gel column chromatography (DCM:MeOH (v/v)=20:1), to afford compound 1E (8.3 g, yield: 80%).

LC-MS (ESI): m/z=468.2 $[M+H]^+$.

Step 5

Compound 1E (2.8 g, 6 mmol), 2-(2-bromoethyl)isoindoline-1,3-dione (9.15 g, 36 mmol), potassium carbonate (7.45 g, 54 mmol) and sodium iodide (5.4 g, 36 mmol) were successively added to dry 2-butanone (60 mL), and the mixture was reacted under nitrogen protection at 95° C. for 48 hours. After the reaction was completed, the reaction liquid was cooled to room temperature and filtered, the filter cake was washed with dichloromethane (80 mL), the filtrate was concentrated under reduced pressure, and the resulting residue was separated by silica gel column chromatography (petroleum ether:ethyl acetate (v/v)=1:0-1:1), to afford target compound 1F (0.92 g, yield: 24%).

LC-MS (ESI): m/z=641.2 [M+H]$^+$.

Step 6

Compound 1F (0.92 g, 1.44 mmol) was dissolved in ethyl acetate (20 mL), palladium on carbon (0.5 g) was added, and the mixture was reacted under hydrogen atmosphere at room temperature for 1 hour. After the reaction was completed, the reaction liquid was filtered, the filter cake was washed with methanol (30 mL), and the filtrate was concentrated under reduced pressure, to afford target compound 1G (0.58 g, yield: 73%).

LC-MS (ESI): m/z=551.2 [M+H]$^+$.

Step 7

Compound 1G (0.58 g, 1.05 mmol) was dissolved in DMF (10 mL), potassium carbonate (0.29 g, 2.1 mmol) was added, the mixture was uniformly stirred, and then deuterated iodomethane (0.30 g, 2.1 mmol) was added dropwise. After the dropwise addition was completed, the mixture was reacted at room temperature for 1 hour. After the reaction was completed, saturated sodium chloride aqueous solution (50 mL) was added, and the mixture was extracted with dichloromethane (50 ml×2). The organic phases were combined, washed with saturated sodium chloride solution (60 mL), dried over anhydrous sodium sulfate, filtered and concentrated, and the residue was separated by silica gel column chromatography (petroleum ether:ethyl acetate (v/v)=1:0-1:1), to afford compound 1H (0.52 g, yield: 87%).

LC-MS (ESI): m/z=568.2 [M+H]$^+$.

Step 8

Compound 1H (0.52 g, 0.92 mmol) was dissolved in trichloromethane (10 mL) and ethanol (10 mL), hydrazine hydrate (0.3 g, 80 wt %) was added, and the mixture was uniformly stirred and reacted at room temperature for 24 hours. After the reaction was completed, the reaction liquid was filtered, the filtrate was concentrated under reduced pressure, and the residue was separated by silica gel column chromatography (dichloromethane:methanol (v/v)=1:0-5:1), to afford compound 11 (0.35 g, yield: 87%).

LC-MS (ESI): m/z=438.1 [M+H]$^+$

Step 9

Compound 11 (0.22 g, 0.50 mmol) was dissolved in water (10 mL), 1 N hydrochloric acid (1 mL) was added, and the mixture was uniformly stirred and heated to 80° C. A solution of potassium cyanate (81 mg, 1 mmol) in water (1 mL) was added dropwise to the reaction. After the dropwise addition was completed, the mixture was reacted at 80° C. for additional 2 h. The reaction liquid was cooled to room temperature, saturated sodium bicarbonate aqueous solution (10 mL) was added, and the mixture was extracted with dichloromethane (20 mL×2). The organic phases were combined, dried over anhydrous sodium sulfate and filtered, the filtrate was concentrated under reduced pressure, and the residue was separated by silica gel column chromatography (dichloromethane:methanol (v/v)=1:0-10:1), to afford compound 1 (0.12 g, yield: 50%).

LC-MS (ESI): m/z=481.3 [M+H]$^+$ $^1$H NMR (400 MHz, $CDCl_3$) δ 6.91 (s, 2H), 6.68 (s, 2H), 5.47 (s, 1H), 5.25 (br, 2H), 4.44 (s, 2H), 4.08 (s, 2H), 3.75 (s, 3H), 3.55 (s, 2H), 2.94 (s, 2H), 2.29 (s, 3H), 2.09 (s, 6H), 1.61 (br, 1H).

Example 2

(E)-1-(2-(2-((2,6-dimethyl-4-(trifluoromethyl)phenyl)imino)-9,10-dimethoxy-4-oxo-6,7-dihydro-2H-pyrimido[6,1-a]isoquinolin-3(4H)-yl)ethyl)urea (Compound 2)

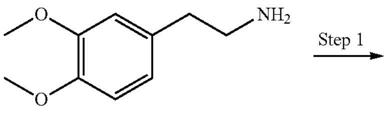

2A

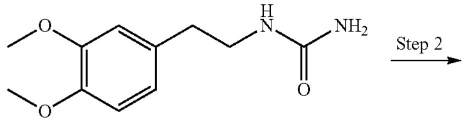

2B

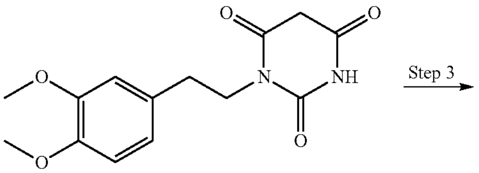

2C

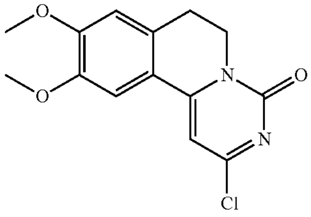

2D

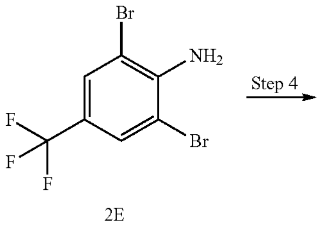

2E

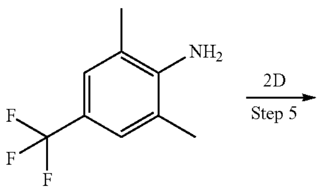

2F

-continued

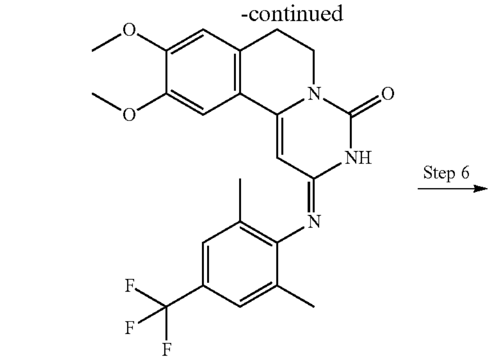

2G

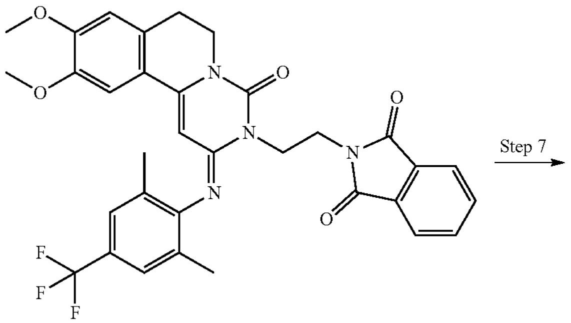

2H

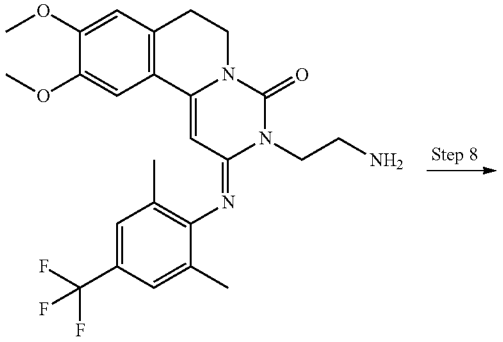

2I

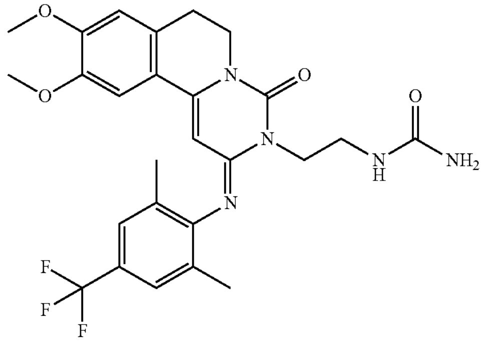

Compound 2

Step 1

2A (50 g, 0.28 mol) was dissolved in water (150 mL), KCNO (8.1 g, 0.10 mol) was added, and then hydrogen chloride solution (40 ml of concentrated hydrochloric acid dissolved in 150 ml of water) was slowly added dropwise. The reaction was heated to reflux and stirred overnight. After the reaction was completed, the reaction liquid was cooled to 0° C. and filtered, the filter cake was washed with cold water (150 mL), and the resulting filter cake was dried, to afford title compound 2B (51 g, 82.3%).

LC-MS (ESI): m/z=225.2 $[M+H]^+$.

Step 2

2B (51 g, 0.22 mol) was dissolved in anhydrous ethanol (300 mL), diethyl malonate (50 g, 0.34 mol) and sodium ethoxide (47 g, 0.69 mol) were successively added, and the reaction was heated to reflux and stirred overnight. After the reaction was completed, the reaction liquid was cooled to room temperature and concentrated under reduced pressure to remove most of ethanol, water (150 mL) was added to the residue, the mixture was adjusted to pH 6.0 with dilute hydrochloric acid (5 M) and filtered, and the filter cake was washed with cold water (150 mL) and dried, to afford title compound 2C (45.0 g, 65.9%).

LC-MS (ESI): m/z=293.3 $[M+H]^+$.

Step 3

2C (20.0 g, 68.4 mmol) was dissolved in $POCl_3$ (200 mL), and the mixture was heated to 100° C. and stirred overnight. After the reaction was completed, the reaction liquid was cooled to room temperature, concentrated to 30 mL and slowly poured into ice water (300 mL), and the mixture was adjusted to pH 6.0 with 5 N sodium hydroxide aqueous solution and extracted with dichloromethane (300 ml×3). The organic phases were combined, dried over anhydrous sodium sulfate, filtered and concentrated, and the residue was separated and purified by silica gel column (dichloromethane:methanol (v/v)=20:1-10:1), to afford title compound 2D (11.5 g, 55%).

$^1H$ NMR (400 MHz, DMSO-$d_6$) δ 7.50 (s, 1H), 7.27 (s, 1H), 7.04 (s, 1H), 4.06-4.03 (m, 2H), 3.86-3.83 (m, 6H), 2.98-2.95 (m, 2H).

LC-MS (ESI): m/z=293.3 $[M+H]^+$.

Step 4

2E (3 g, 9.46 mmol) and trimethylboroxine (1.79 g, 14.2 mmol) were dissolved in ethylene glycol dimethyl ether (12 mL), tetrakis (triphenylphosphine) palladium (1.09 g, 0.95 mmol) and potassium carbonate (3.92 g, 28.38 mmol) were successively added, and the mixture was reacted under nitrogen atmosphere at 100° C. After the reaction was completed, the reaction was terminated, cooled to room temperature and concentrated under reduced pressure to remove most of the reaction liquid, and DCM (20 mL) was added to the residue. The mixture was filtered over diatomaceous earth, the filtrate was concentrated under reduced pressure, and the residue was separated and purified by silica gel column (dichloromethane:methanol (v/v)=20:1-10:1), to afford title compound 2F (0.42 g, 25%).

LC-MS (ESI): m/z=190.2 $[M+H]^+$.

Step 5

2D (0.5 g, 1.71 mmol) was dissolved in isopropanol (12 mL), 2F (0.49 g, 2.57 mmol) was added, and after the addition was completed, the mixture was reacted at 90° C. for 24 hours. After the reaction was completed, the reaction was terminated, cooled to room temperature and concentrated under reduced pressure to remove most of the reaction solvent, saturated sodium bicarbonate aqueous solution (20 mL) was added to the residue, and the mixture was extracted with dichloromethane (20 mL×3). The organic phases were combined, washed with saturated sodium chloride aqueous solution (20 mL), dried over anhydrous sodium sulfate, filtered and concentrated, and the residue was separated by silica gel column chromatography (DCM:MeOH (v/v)=20:1), to afford compound 2G (0.65 g, yield: 85%).

LC-MS (ESI): m/z=446.3 $[M+H]^+$.

Step 6

Compound 2G (0.4 g, 0.9 mmol), 2-(2-bromoethyl) isoindoline-1,3-dione (0.69 g, 2.7 mmol), potassium carbonate (0.37 g, 2.7 mmol) and sodium iodide (0.41 g, 2.7 mmol) were successively dissolved in dry acetonitrile (20 mL), and the mixture was reacted under nitrogen protection and microwave at 120° C. for 2 hours. After the reaction was completed, the reaction liquid was cooled to room temperature and filtered, the filter cake was washed with dichloromethane (20 mL), the filtrate was concentrated under reduced pressure, and the resulting residue was separated by silica gel column chromatography (petroleum ether:ethyl acetate (v/v)=1:0-1:1), to afford target compound 2H (0.25 g, yield: 45%).

LC-MS (ESI): m/z=619.3 $[M+H]^+$.

Step 7

Compound 2H (0.25 g, 0.40 mmol) was dissolved in trichloromethane (10 mL) and ethanol (10 mL), hydrazine hydrate (0.2 g, 80 wt %) was added, and the mixture was uniformly stirred and reacted at room temperature for 24 hours. After the reaction was completed, the reaction liquid was filtered, the filtrate was concentrated under reduced pressure, and the residue was separated by silica gel column chromatography (dichloromethane:methanol (v/v)=1:0-5:1), to afford compound 21 (0.17 g, yield: 89%).

LC-MS (ESI): m/z=489.1 $[M+H]^+$.

Step 8

Compound 21 (0.17 g, 0.36 mmol) was dissolved in water (10 mL), 1 N hydrochloric acid (1 mL) was added, and the mixture was uniformly stirred and heated to 80° C. A solution of potassium cyanate (81 mg, 1 mmol) in water (1 mL) was added dropwise to the system. After the dropwise addition was completed, the mixture was reacted for additional 2 h. The reaction liquid was cooled to room temperature, saturated sodium bicarbonate aqueous solution (10 mL) was added, and the mixture was extracted with dichloromethane. The organic phases were combined, dried over anhydrous sodium sulfate and filtered, the filtrate was concentrated under reduced pressure, and the residue was separated by silica gel column chromatography (dichloromethane:methanol (v/v)=1:0-10:1), to afford compound 2 (0.08 g, yield: 41%).

$^1H$ NMR (400 MHz, Methanol-$d_4$) δ 7.36 (s, 2H), 6.88 (s, 1H), 6.74 (s, 1H), 5.38 (s, 1H), 4.38-4.35 (s, 2H), 4.18-3.93 (m, 2H), 3.86 (s, 3H), 3.66 (s, 3H), 3.56-3.53 (m, 2H), 2.94-2.91 (m, 2H), 2.16 (s, 6H).

LC-MS (ESI): m/z=532.3 $[M+H]^+$.

Example 3

(E)-1-(2-(2-((4-cyclopropyl-2,6-dimethylphenyl)imino)-9,10-dimethoxy-4-oxo-6,7-dihydro-2H-pyrimido[6,1-a]isoquinolin-3(4H)-yl)ethyl)urea (Compound 3)

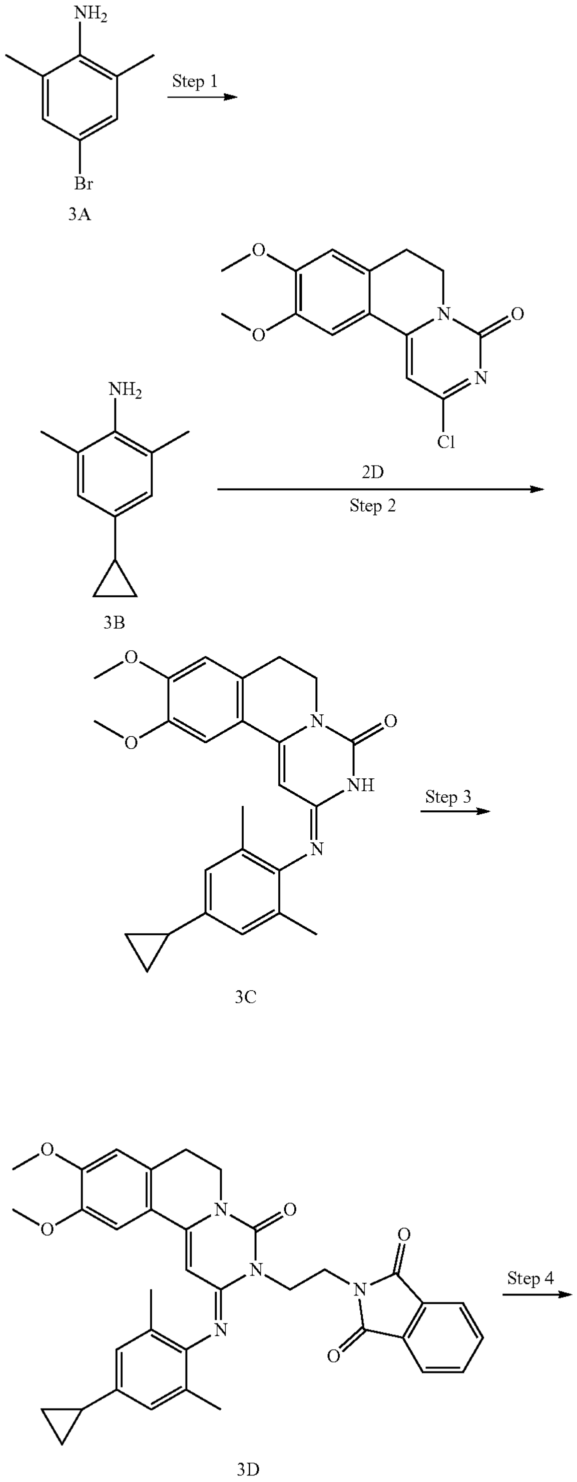

-continued

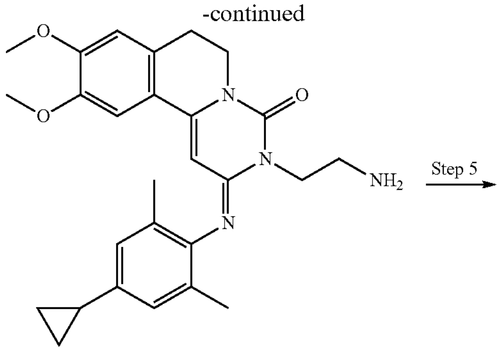

3E

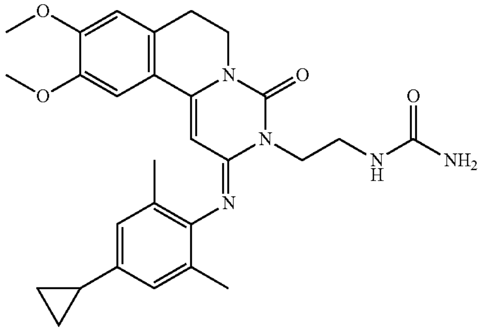

Compound 3

Step 1

Compound 3A (3 g, 15.07 mmol) and cyclopropylboronic acid (1.94 g, 22.67 mmol) were dissolved in toluene (20 mL) and water (5 mL), palladium acetate (0.34 g, 1.51 mmol), tricyclohexylphosphine (0.47 g, 28.38 mmol) and potassium phosphate (6.40 g, 30.14 mmol) were successively added, and the mixture was reacted under nitrogen atmosphere at 100° C. After the reaction was completed as monitored by TLC and LC-MS, the reaction was terminated, cooled to room temperature and concentrated under reduced pressure to remove most of the reaction liquid, and DCM (20 mL) was added to the residue. The mixture was filtered over diatomaceous earth, the filtrate was concentrated under reduced pressure, and the residue was separated and purified by silica gel column (dichloromethane:methanol (v/v)=20:1-10:1), to afford title compound 3B (0.70 g, 29%).

LC-MS (ESI): m/z=162.2 $[M+H]^+$.

Step 2

2D (0.5 g, 1.71 mmol) was dissolved in isopropanol (12 mL), 3B (0.41 g, 2.57 mmol) was added, and after the addition was completed, the mixture was reacted at 90° C. for 24 hours. After the reaction was completed, the reaction liquid was cooled to room temperature and concentrated under reduced pressure, saturated sodium bicarbonate aqueous solution (20 mL) was added, and the mixture was extracted with dichloromethane (20 mL×3). The organic phases were combined, washed with saturated sodium chloride aqueous solution (20 mL), dried over anhydrous sodium sulfate and filtered, the filtrate was concentrated under reduced pressure, and the residue was separated by silica gel column chromatography (DCM:MeOH (v/v)=20:1), to afford compound 3C (0.50 g, yield: 70%).

LC-MS (ESI): m/z=418.3 $[M+H]^+$.

Step 3

Compound 3C (0.50 g, 1.20 mmol), 2-(2-bromoethyl) isoindoline-1,3-dione (0.92 g, 3.6 mmol), potassium carbonate (0.50 g, 3.6 mmol) and sodium iodide (0.54 g, 3.6 mmol) were dissolved in dry acetonitrile (20 mL), and the mixture was reacted under nitrogen atmosphere and microwave at 120° C. for 2 hours. After the reaction was completed, the reaction liquid was cooled to room temperature and filtered, the filter cake was washed with dichloromethane (20 mL), the filtrate was concentrated under reduced pressure, and the resulting residue was separated by silica gel column chromatography (petroleum ether:ethyl acetate (v/v)=1:0-1:1), to afford target compound 3D (0.33 g, yield: 47%).

LC-MS (ESI): m/z=591.3 $[M+H]^+$.

Step 4

Compound 3D (0.33 g, 0.56 mmol) was dissolved in trichloromethane (10 mL) and ethanol (10 mL), hydrazine hydrate (0.3 g, 80 wt %) was added, and the mixture was uniformly stirred and reacted at room temperature for 24 hours. After the reaction was completed, the reaction liquid was filtered, the filtrate was concentrated under reduced pressure, and the residue was separated by silica gel column chromatography (dichloromethane:methanol (v/v)=1:0-5:1), to afford compound 3E (0.18 g, yield: 70%).

LC-MS (ESI): m/z=461.2 $[M+H]^+$.

Step 5

Compound 3E (0.18 g, 0.39 mmol) was dissolved in water (10 mL), 1 N hydrochloric acid (1 mL) was added, and the mixture was uniformly stirred and heated to 80° C. A solution of potassium cyanate (81 mg, 1 mmol) in water (1 mL) was added dropwise to the system. After the dropwise addition was completed, the mixture was stirred for additional 2 h. The reaction liquid was cooled to room temperature, saturated sodium bicarbonate aqueous solution (10 mL) was added, and the mixture was extracted with dichloromethane (20 mL×3). The organic phases were combined, dried over anhydrous sodium sulfate and filtered, the filtrate was concentrated under reduced pressure, and the residue was separated by silica gel column chromatography (dichloromethane:methanol (v/v)=1:0-10:1), to afford compound 3 (0.07 g, yield: 36%).

$^1$H NMR (400 MHz, Methanol-$d_4$) δ 7.03-6.98 (m, 3H), 6.79 (s, 1H), 5.65 (s, 1H), 4.39-4.36 (m, 2H), 4.19-4.16 (m, 2H), 3.91 (s, 3H), 3.69 (s, 3H), 3.56-3.52 (m, 2H), 3.06-3.03 (m, 2H), 2.27 (s, 6H), 1.94-1.91 (m, 1H), 1.16-0.94 (m, 2H), 0.83-0.61 (m, 2H).

LC-MS (ESI): m/z=504.3 $[M+H]^+$.

Example 4

(E)-1-(2-(9-ethoxy-2-(mesitylimino)-10-methoxy-4-oxo-6,7-dihydro-2H-pyrimido[6,1-a]isoquinolin-3(4H)-yl)ethyl)urea (Compound 4)

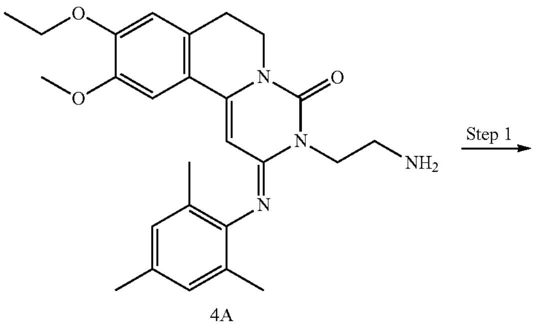

4A

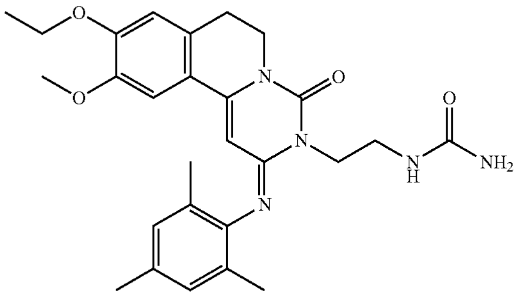

Compound 4

Step 1

Compound 4A (77 mg, 0.17 mmol) (compound 4A synthesized with reference to patent WO 2021143843) was dissolved in water (5 mL), potassium cyanate (48.3 mg, 0.6 mmol, 3.5 eq) and dilute hydrochloric acid (conc. HCl (43 ul, 0.51 mmol, 3 eq) diluted with water (5 mL)) were added, and after the addition was completed, the mixture was heated to 100° C. and reacted for 18 hours. After raw materials were completely reacted as monitored by TLC/LCMS, the reaction liquid was cooled to room temperature and extracted 3 times with dichloromethane (20 mL), the organic phases were combined, dried over anhydrous sodium sulfate, filtered and concentrated under reduced pressure, and the resulting crude product was purified by silica gel column chromatography (dichloromethane:methanol (v/v)=10:1), to afford compound 4 (81 mg, 0.16 mmol, yield: 97%).

LC-MS (ESI): m/z=492.2 $[M+H]^+$.

$^1H$ NMR (400 MHz, Chloroform-d) δ 6.94 (s, 2H), 6.68 (m, 2H), 5.49 (s, 1H), 4.47 (s, 2H), 4.15 (m, 2H), 4.11 (m, 2H), 3.74 (s, 3H), 3.58 (s, 2H), 2.95 (s, 2H), 2.30 (s, 3H), 2.13 (s, 6H), 1.49 (m, 3H).

Example 5

(E)-1-(2-(2-((4-fluoro-2,6-dimethylphenyl)imino)-9,10-dimethoxy-4-oxo-6,7-dihydro-2H-pyrimido[6,1-a]isoquinolin-3(4H)-yl)ethyl)urea (Compound 5)

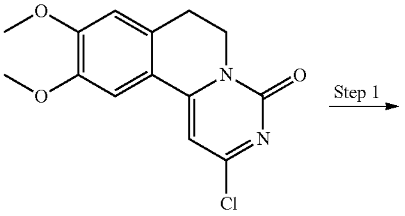

2D

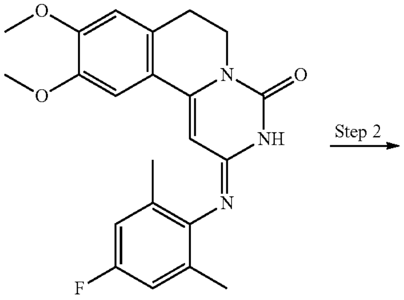

5A

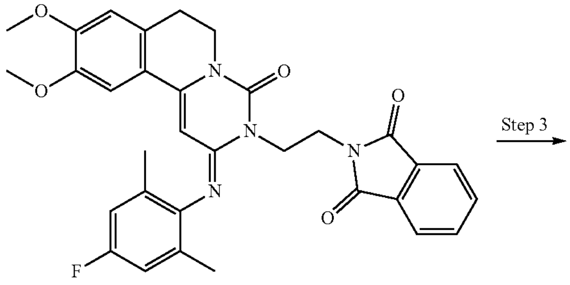

5B

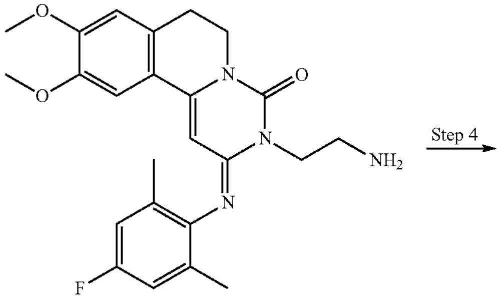

5C

-continued

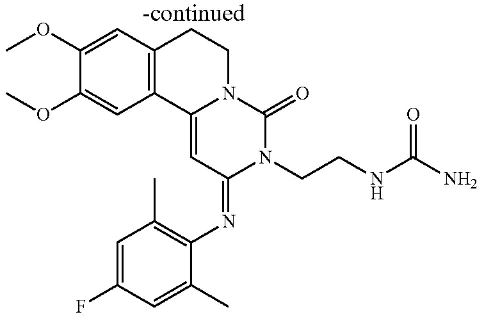

Compound 5

Step 1

2D (0.5 g, 1.71 mmol) was dissolved in isopropanol (12 mL), 4-fluoro-2-methylaniline (0.32 g, 2.57 mmol) was added, and after the addition was completed, the mixture was reacted at 90° C. for 12 hours. After the reaction was completed, the reaction liquid was cooled to room temperature and concentrated under reduced pressure, saturated sodium bicarbonate aqueous solution (20 mL) was added to the residue, and the mixture was extracted with dichloromethane (20 mL×3). The organic phases were combined, washed with saturated sodium chloride aqueous solution (20 mL), dried over anhydrous sodium sulfate and filtered, the filtrate was concentrated under reduced pressure, and the residue was separated by silica gel column chromatography (DCM:MeOH (v/v)=20:1), to afford compound 5A (0.57 g, yield: 85%).

LC-MS (ESI): m/z=396.2 $[M+H]^+$.

Step 2

Compound 5A (0.57 g, 1.5 mmol), 2-(2-bromoethyl) isoindoline-1,3-dione (1.15 g, 4.5 mmol), potassium carbonate (0.62 g, 4.5 mmol) and sodium iodide (0.69 g, 4.5 mmol) were dissolved in dry acetonitrile (20 mL), and the mixture was reacted under nitrogen protection and microwave at 120° C. for 2 hours. After the reaction was completed, the reaction liquid was cooled to room temperature and filtered, the filter cake was washed with dichloromethane (20 mL), the filtrate was concentrated under reduced pressure, and the resulting residue was separated by silica gel column chromatography (petroleum ether:ethyl acetate (v/v)=1:0-1:1), to afford target compound 5B (0.34 g, yield: 40%).

LC-MS (ESI): m/z=569.2 $[M+H]^+$.

Step 3

Compound 5B (0.34 g, 0.60 mmol) was dissolved in trichloromethane (10 mL) and ethanol (10 mL), hydrazine hydrate (0.30 g, 80 wt %) was added, and the mixture was uniformly stirred and reacted at room temperature for 12 hours. After the reaction was completed, the reaction liquid was filtered, the filtrate was concentrated under reduced pressure, and the residue was separated by silica gel column chromatography (dichloromethane:methanol (v/v)=1:0-5:1), to afford compound 5C (0.17 g, yield: 89%).

LC-MS (ESI): m/z=439.1 $[M+H]^+$.

Step 4

Compound 5C (0.085 g, 0.2 mmol) was dissolved in water (10 mL), 1 N hydrochloric acid (1 mL) was added, and the mixture was uniformly stirred and heated to 80° C. A solution of potassium cyanate (81 mg, 1 mmol) in water (1 mL) was added dropwise to the system. After the dropwise addition was completed, the mixture was stirred for additional 2 h under this condition. The reaction liquid was cooled to room temperature, saturated sodium bicarbonate aqueous solution (10 mL) was added, and the mixture was extracted with dichloromethane (20 mL×2). The organic phases were combined, dried over anhydrous sodium sulfate and filtered, the filtrate was concentrated under reduced pressure, and the residue was separated by silica gel column chromatography (dichloromethane:methanol (v/v)=1:0-10:1), to afford compound 5 (0.09 g, yield: 93%).

$^1$H NMR (400 MHz, $CD_3OD$) δ 6.78 (s, 1H), 6.74 (s, 1H), 6.71 (s, 1H), 6.64 (s, 1H), 5.35 (s, 1H), 4.26-4.23 (m, 2H), 3.92-3.89 (m, 2H), 3.76 (s, 3H), 3.59 (s, 3H), 3.45-3.42 (m, 2H), 2.84-2.81 (m, 2H), 1.99 (s, 6H).

LC-MS (ESI): m/z=482.3 $[M+H]^+$.

Example 6

(E)-1-(2-(9-(benzyloxy)-2-(mesitylimino)-10-methoxy-4-oxo-6,7-dihydro-2H-pyrimido[6,1-a]isoquinolin-3(4H)-yl)ethyl)urea (Compound 6)

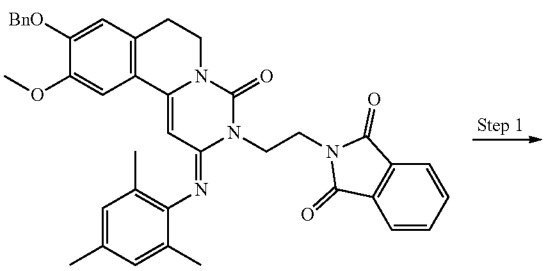

1F

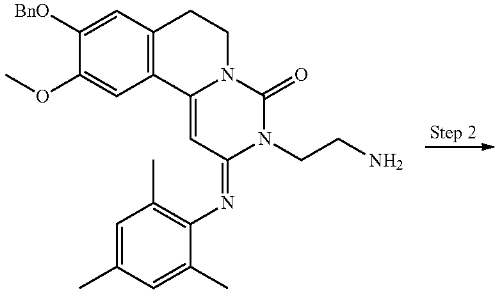

6A

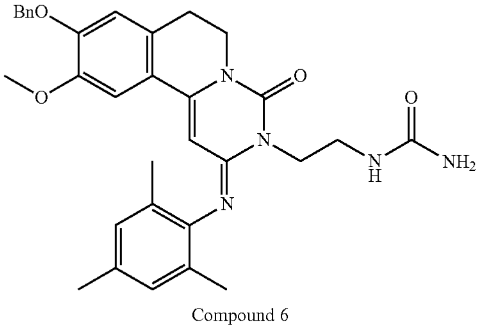

Compound 6

Step 1

Compound 1F (0.2 g, 0.31 mmol) was dissolved in trichloromethane (10 mL) and ethanol (10 mL), hydrazine hydrate (194 mg, 3.1 mmol, 10 eq, 80% w/w) was added, and the mixture was reacted overnight at room temperature. After the reaction was completed as monitored by TLC/LCMS, the reaction was quenched with saturated sodium bicarbonate aqueous solution (30 mL), and the mixture was extracted with dichloromethane (40 mL×2). The organic phases were combined, dried over anhydrous sodium sulfate, filtered and concentrated under reduced pressure, and the resulting crude product was purified by silica gel column chromatography (dichloromethane:methanol=10:1), to afford product 6A (63 mg, 0.12 mmol, yield: 40%).

Step 2

Compound 6A (63 mg, 0.12 mmol) was dissolved in water (5 mL), potassium cyanate (34 mg, 0.42 mmol, 3.5 eq) and concentrated hydrochloric acid (0.03 mL, 0.36 mmol, 3 eq) diluted with water (5 mL) were added, and after the addition was completed, the mixture was heated to 100° C. and reacted overnight. After the reaction was completed as monitored by TLC/LCMS, the reaction liquid was cooled to room temperature, quenched with saturated sodium bicarbonate aqueous solution (20 mL), and extracted with dichloromethane (20 mL×2). The organic phases were combined, dried over anhydrous sodium sulfate, filtered and concentrated, and the resulting residue was separated and purified by silica gel column chromatography (dichloromethane: methanol=10:1), to afford compound 6 (51 mg, 0.09 mmol, yield: 77%).

LC-MS (ESI): m/z=554.3 $[M+H]^+$.

$^1H$ NMR (400 MHz, $CDCl_3$) δ 7.41-7.33 (m, 5H), 6.92 (s, 2H), 6.72 (s, 2H), 5.48 (s, 1H), 5.18 (s, 2H), 4.44 (m, 2H), 4.06 (m, 2H), 3.76 (s, 3H), 3.56 (m, 2H), 2.89 (m, 2H), 2.30 (s, 3H), 2.08 (s, 6H).

Example 7

(E)-1-(2-(2-(mesitylimino)-9-methoxy-10-(methoxy-d3)-4-oxo-6,7-dihydro-2H-pyrimido[6,1-a]isoquinolin-3 (4H)-yl)ethyl)urea (Compound 7)

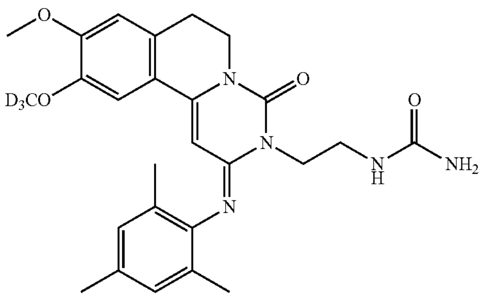

Compound 7

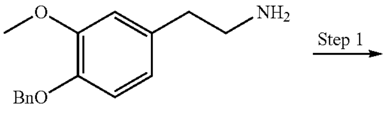

7A

-continued

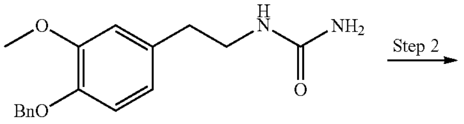

7B

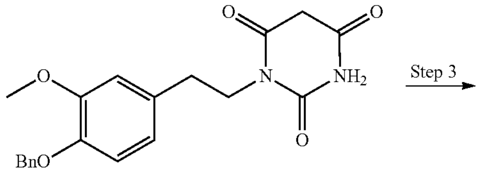

7C

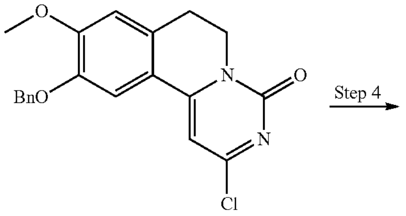

7D

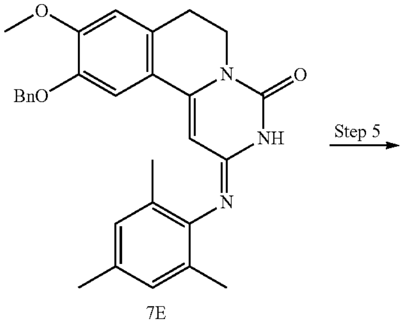

7E

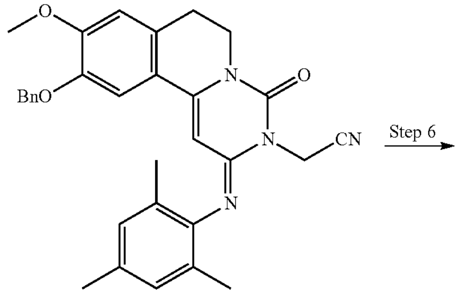

7F

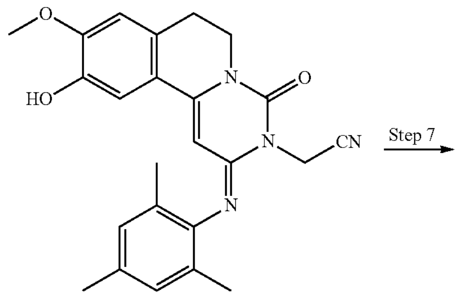

7G

-continued

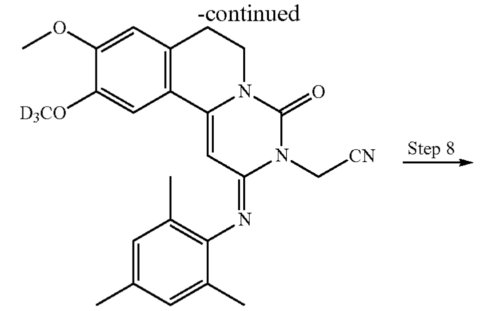

7H

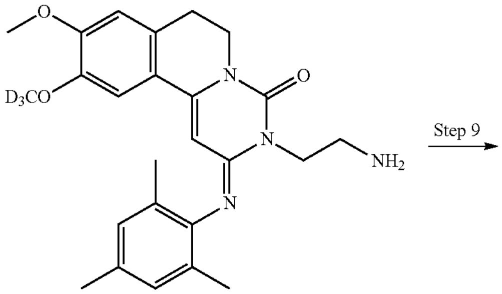

7I

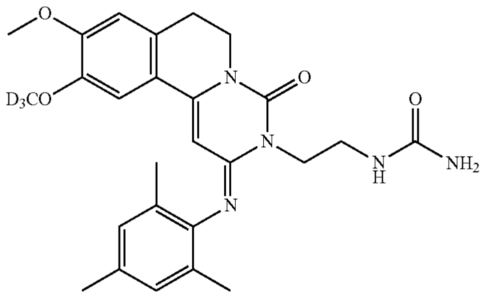

Compound 7

Step 1

Compound 2-(4-(benzyloxy)-3-methoxyphenyl) ethanamine (7A) (synthesized with reference to the content described in Bioorganic & Medicinal Chemistry, 21 (4), 856-868.) (51.5 g, 0.20 mol) was dissolved in water (300 mL), potassium cyanate (32.4 g, 0.40 mol) was added portionwise, the mixture was uniformly stirred, and then 2N hydrochloric acid (240 mL) was added dropwise. After the dropwise addition was completed, the mixture was refluxed and reacted overnight. The reaction liquid was cooled to 0° C. and filtered, and the filter cake was rinsed with ice ethanol and dried, to afford target compound 7B (38.0 g, yield: 63%).

LC-MS (ESI): m/z=301.2 $[M+H]^+$.

Step 2

Compound 7B (38 g, 0.13 mol) was dissolved in anhydrous ethanol (300 mL), diethyl malonate (27 g, 0.17 mol) was added, the mixture was uniformly stirred, and then sodium ethoxide (133 g, 0.39 mol, 20 wt % in EtOH) was added dropwise. After the dropwise addition was completed, the mixture was refluxed and reacted overnight. The reaction liquid was cooled to room temperature, concentrated to 150 ml under reduced pressure, diluted with water (150 mL), adjusted to pH 6.0 with 5N hydrochloric acid and filtered, and the filter cake was washed with water (150 mL) and dried, to afford target compound 7C (42 g, yield: 90%).

LC-MS (ESI): m/z=369.1 $[M+H]^+$.

Step 3

Compound 7C (42 g, 114 mmol) was dissolved in phosphorus oxychloride (300 mL), and the mixture was reacted overnight at 120° C. After the reaction was completed, the reaction liquid was cooled to room temperature and concentrated under reduced pressure, the residue was slowly added to ice water (300 mL), and saturated sodium bicarbonate aqueous solution was added to adjust to pH=6.0. The mixture was extracted with dichloromethane (500 mL×3), the organic phases were combined, dried over anhydrous sodium sulfate and filtered, the filtrate was concentrated under reduced pressure, and the resulting crude product was separated by silica gel column chromatography (DCM: MeOH (v/v)=40:1), to afford target compound 7D (12.7 g, yield: 30%).

LC-MS (ESI): m/z=369.1 $[M+H]^+$.

Step 4

7D (0.82 g, 2.22 mmol) was dissolved in isopropanol (120 mL), 2,4,6-trimethylaniline (0.446 g, 3.3 mmol) was added, and after the addition was completed, the mixture was reacted at 90° C. for 24 hours. After the reaction was completed, the reaction liquid was cooled to room temperature and concentrated under reduced pressure, saturated sodium bicarbonate aqueous solution (100 mL) was added to the residue, and the mixture was extracted with dichloromethane (100 mL×3). The organic phases were combined, washed with saturated sodium chloride aqueous solution (100 mL), dried over anhydrous sodium sulfate and filtered, the filtrate was concentrated under reduced pressure, and the residue was separated by silica gel column chromatography (DCM:MeOH (v/v)=20:1), to afford compound 7E (0.53 g, yield: 55%).

LC-MS (ESI): m/z=468.2 $[M+H]^+$.

Step 5

Compound 7E (0.53 g, 1.13 mmol), bromoacetonitrile (0.54 g, 3.9 mmol) and lithium carbonate (0.69 g, 3.3 mmol) were successively dissolved in dry acetonitrile (10 mL), and the mixture was reacted under nitrogen atmosphere at 90° C. for 18 hours. After the reaction was completed, the reaction liquid was cooled to room temperature and filtered, the filter cake was washed with dichloromethane (80 mL), the filtrate was concentrated under reduced pressure, and the resulting crude product was separated by silica gel column chromatography (dichloromethane:methanol (v/v)=1:0-20:1), to afford target compound 7F (0.5 g, yield: 42%).

LC-MS (ESI): m/z=507.3 $[M+H]^+$.

Step 6

Compound 7F (0.5 g, 1.0 mmol) was dissolved in ethyl acetate (50 mL), palladium on carbon (0.3 g, 10% w/w) was added, and the mixture was reacted under hydrogen atmosphere at room temperature for 3 hours. After raw materials were completely reacted as monitored by TLC/LCMS, the reaction liquid was filtered to remove palladium on carbon, the filter cake was washed twice with ethyl acetate (20 mL), the filtrate was concentrated under reduced pressure, and the resulting crude product was purified by silica gel column chromatography (petroleum ether:ethyl acetate=3:1), to afford compound 7G (0.21 g, yield: 58%).

LC-MS (ESI): m/z=417.3 $[M+H]^+$.

Step 7

Compound 7G (210 mg, 0.64 mmol) was dissolved in DMF (20 mL), deuterated iodomethane (186 mg, 1.28 mmol) and potassium carbonate (177 mg, 1.28 mmol) were successively added, and the mixture was stirred at room temperature for 5 hours. After raw materials were completely reacted as monitored by TLC/LCMS, the reaction was quenched with saturated sodium chloride aqueous solution (30 mL), and the mixture was extracted with dichloromethane (40 mL×2). The organic phases were combined, dried over anhydrous sodium sulfate, filtered and concentrated under reduced pressure, and the resulting crude product was purified by silica gel column chromatography (petroleum ether:ethyl acetate=3:1), to afford compound 7H (180 mg, yield: 64%).

LC-MS (ESI): m/z=434.2 $[M+H]^+$.

Step 8

Compound 7H (180 mg, 0.414 mmol) was added to ethanol (10 mL), Raney Nickel (150 mg) was added portionwise at room temperature, hydrazine hydrate (1 mL) was added, and the mixture was heated to 60° C. and reacted for 1 hour. After the reaction was completed, the reaction liquid was cooled to room temperature, and the filtrate was concentrated under reduced pressure, to afford compound 71 (0.12 g, yield: 66%), which was directly used in the next reaction without further purification.

LC-MS (ESI): m/z=438.2 $[M+H]^+$.

Step 9

Compound 71 (0.12 g, 0.23 mmol) was dissolved in water (10 mL), 1 N hydrochloric acid (1 mL) was added, and the mixture was uniformly stirred and heated to 80° C. A solution of potassium cyanate (81 mg, 1 mmol) in water (1 mL) was added dropwise to the system. After the dropwise addition was completed, the mixture was stirred for additional 2 h under this condition. The reaction liquid was cooled to room temperature, saturated sodium bicarbonate (10 mL) was added, and the mixture was extracted with dichloromethane (30 mL×2). The organic phases were combined, dried over anhydrous sodium sulfate and filtered, the filtrate was concentrated under reduced pressure, and the residue was separated by silica gel column chromatography (dichloromethane:methanol (v/v)=1:0-10:1), to afford compound 7 (0.08 g, yield: 41%).

LC-MS (ESI): m/z=481.3 $[M+H]^+$.

$^1$H NMR (400 MHz, Methanol-$d_4$) δ 6.80 (s, 2H), 6.77 (s, 1H), 6.65 (s, 1H), 5.40 (s, 1H), 4.25-4.22 (m, 2H), 3.91-3.88 (m, 2H), 3.76 (s, 3H), 3.45-3.42 (m, 2H), 2.83-2.81 (m, 1H), 2.17 (s, 3H), 1.96 (s, 6H).

Biological Test

1. In Vitro Assay of the Inhibitory Activity of Compounds Against PDE 3A and PDE 4B2 Enzymes Experimental Materials:
- Envision 2104 Multilabel Reader (PerkinElmer)
- Black 96-well Plate (Cat #6005540, PerkinElmer)
- PDE3A Assay Kit (BPS, Cat. 79736), PDE4B2 Assay Kit (BPS, Cat. 60343)
  - PDE3A recombinant enzyme
  - PDE4B2 recombinant enzyme
  - FAM-Cyclic-3', 5'-AMP
  - PDE assay buffer.
  - Binding Agent
- Binding Agent Diluent (cAMP)

Experimental Steps:
1) Prepare FAM CAMP working solution: 20 μL of FAM-Cyclic-3', 5'-AMP stock was added to 1980 μL of PDE assay buffer. The mixture was added to all wells at 25 μL/well.
2) Prepare compound solution: the test compounds were dissolved in DMSO to make a 10 mM stock solution. The compound stock solution was diluted in DMSO to a 100× Top Dose diluent. 5 μL of 100× Top Dose diluent was added to 45 μL of PDE assay buffer to prepare a compound Top Dose working solution. Then, the compound working solution was subjected to double dilution with PDE assay buffer containing 10% DMSO to prepare compound working solutions of various concentrations. The compound working solutions were added to compound wells at 5 μL/well. 5 μL of PDE assay buffer containing 10% DMSO was added to each control well.
3) Prepare PDE enzyme solution: PDE3A and PDE4B2 enzyme stock solutions were diluted to 150 pg/μL and 50 pg/μL, respectively, with PDE assay buffer, and added to all compound wells and Vehicle control wells at 20 μL/well. 20 μL of PDE assay buffer was added to Blank control wells.
4) React at room temperature for 1 h.
5) Prepare Binding Agent: 80 μL of binding agent was added to 7920 μL of binding agent diluent, and the mixture was mixed well and added to all wells at 100 μL/well.
6) React at room temperature for 1 h.
7) Read FP on Envision.
8) Calculation formula for original data:

$$\%\ \text{Inhibition rate} = (FP_v - FP_s)/(FP_v - FP_s) \times 100\%$$

$FP_S$=sample FP
$FP_V$=Vehicle control FP
$FP_B$=Blank control FP.

Nonlinear regression analysis of log[dose]-inhibition rate was performed by graphpad and IC50 was calculated.

Experimental Results:

The compounds of the present invention had excellent PDE 3 and PDE 4 inhibitory activity, with $IC_{50}$ values below 500 nM. Some compounds with good inhibitory activity had $IC_{50}$<200 nM, some compounds with better inhibitory activity had $IC_{50}$<100 nM, and some compounds with excellent inhibitory activity had $IC_{50}$<50 nM. For example, for PDE 3, the $IC_{50}$ of compound 1 was 0.15 nM and the $IC_{50}$ of compound 7 was 0.17 nM. The test results of some compounds are listed in the table below.

TABLE 1

Results of in vitro screening assay of compounds

| Compound | PDE 3A $IC_{50}$ (nM) |
|---|---|
| 1 | A |
| 2 | B |
| 3 | A |
| 4 | A |
| 5 | B |
| 7 | A |

A: 0 nM < $IC_{50}$ ≤ 50 nM;
B: 50 nM < $IC_{50}$ ≤ 100 nM;
C: 100 nM < $IC_{50}$ ≤ 200 nM;
D: 200 nM < $IC_{50}$;
NT: not tested.

2. Study on the Inhibitory Effect of Compounds on Methacholine-Induced Bronchoconstriction in Guinea Pigs Male guinea pigs were selected as test animals in this study. The drug-treated group was orally administered with RPL554, compound 1 and compound 7 at a dose of 10 mg/kg, respectively, and the control group was administered with an equal dose of solvent. The animals were placed in a WBP instrument aerosol chamber 2 h, 4 h and 6 h after drug exposure. After the animals were adapted, they inhaled 300 μL of acetylcholine solution (0.5 mg/mL) by nebulization. After the end of the methacholine (Mch) exposure, Penh values were recorded continuously for 7 minutes. The percentage of bronchoconstriction inhibition by the compounds was calculated based on the Penh values.

The inhibition rate of each compound at an oral dose of 10 mg/kg on bronchoconstriction is shown in the table below:

| Inhibition rate | RPL554 | Compound 1 | Compound 7 |
|---|---|---|---|
| 6 h | 35% | 69% | 80% |

3. Experiment on Guinea Pig Tracheal Rings

Experimental method: guinea pig tracheal rings were placed in a specific culture medium (Krebs-Henseleit) and balanced under 1 g tension for 40 minutes; carbachol was added in an amount sufficient to achieve 100% constriction of the tracheal rings; 1×10^6M of the drug was added to detect changes in the contractile tension of the tracheal rings.

Test conditions: 10 uM single dose, 4 samples in each group, calculate the 50% inhibition onset time and 50% inhibition recovery time at this dose.

| Compound name | $OT_{50}$ (min) | $RT_{50}$ (h) | % inhibition @6.75 h |
|---|---|---|---|
| RPL554 | 25.51 | >6.75 h | 56.70 |
| Compound 7 | 19.97 | >6.75 h | 75.94 |

Conclusion: in this experiment, compound 7 had a shorter onset time and a longer duration of action than RPL554, and its inhibition rate on tracheal constriction at 6.75 h was higher than that of RPL.

Notes: the structure of RPL554 is:

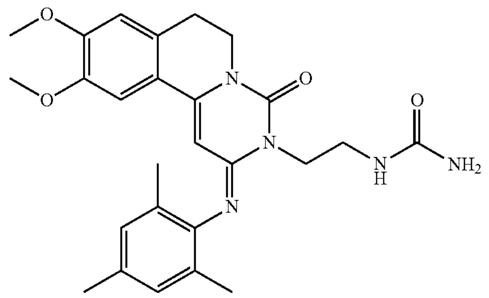 [SMILES: COc1cc2c(cc1OC)-c1c/c(=N\c3c(C)cc(C)cc3C)n(CCNC(N)=O)c(=O)n1CC2]

The invention claimed is:

1. A compound selected from the group consisting of the following structures:

Compound 1

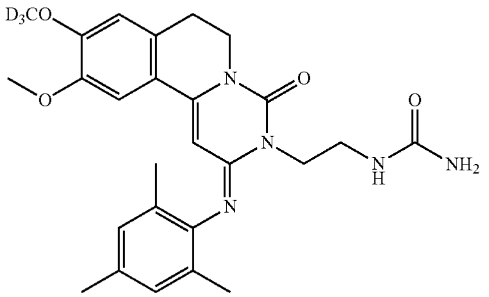

and

Compound 7

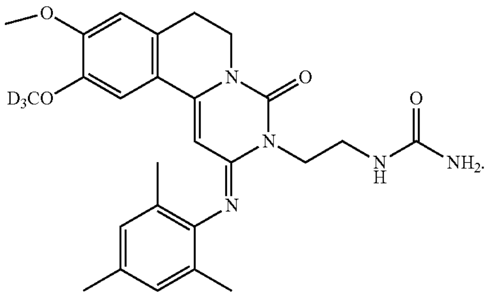

2. A pharmaceutical composition, comprising the compound according to claim 1, and a pharmaceutically acceptable carrier and/or auxiliary agent.

3. A method of treating chronic obstructive pulmonary disease (COPD) or asthma comprising administering the compound according to claim 1 to a subject in need thereof.

4. A method of treating chronic obstructive pulmonary disease (COPD) or asthma comprising administering the pharmaceutical composition according to claim 2 to a subject in need thereof.

5. A compound that has the following structure:

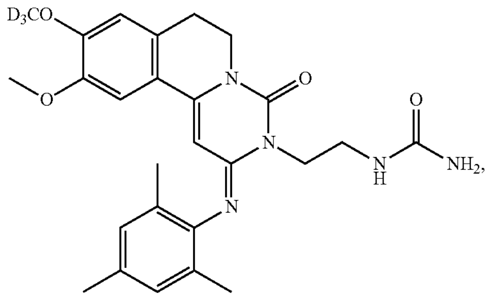

or a pharmaceutically acceptable salt thereof.

6. The compound of claim 5, wherein the compound has the following structure:

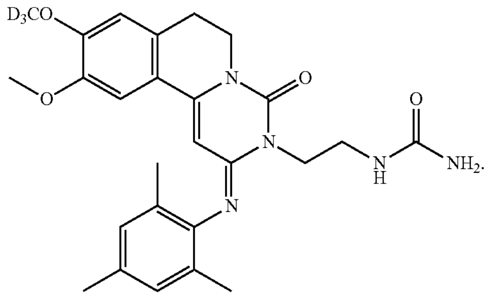

7. A pharmaceutical composition, comprisingthe compound according to claim 5, and a pharmaceutically acceptable carrier and/or auxiliary agent.

8. A pharmaceutical composition, comprising the compound accordingto claim 6, and a pharmaceutically acceptable carrier and/or auxiliary agent.

9. A method of treating chronic obstructive pulmonary disease (COPD) or asthma in a human comprising administering to the human in need thereof a compound that has the following structure:

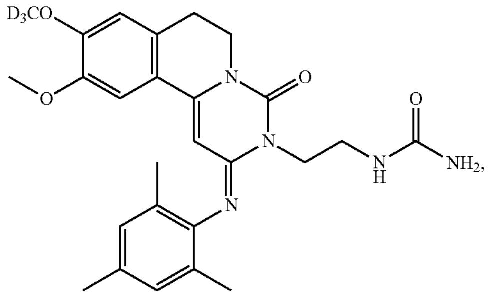

or a pharmaceutically acceptable salt thereof.

10. A method of treating chronic obstructive pulmonary disease (COPD) or asthma in a human comprising administering to the human in need thereof a pharmaceutical composition comprising a compound that has the following structure:

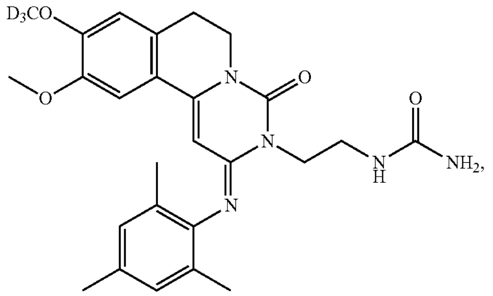

or a pharmaceutically acceptable salt thereof; and a pharmaceutically acceptable carrier and/or auxiliary agent.

11. A compound that has the following structure:

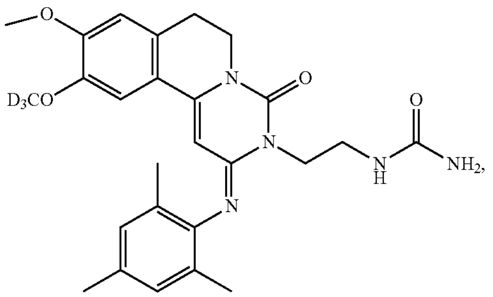

or a pharmaceutically acceptable salt thereof.

12. A compound that has the following structure:

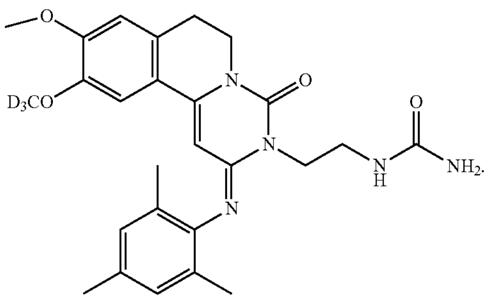

13. A pharmaceutical composition, comprising the compound according to claim 11, and a pharmaceutically acceptable carrier and/or auxiliary agent.

14. A pharmaceutical composition, comprising the compound according to claim 12, and a pharmaceutically acceptable carrier and/or auxiliary agent.

15. A method of treating chronic obstructive pulmonary disease (COPD) in a human comprising administering to the human in need thereof a compound that has the following structure:

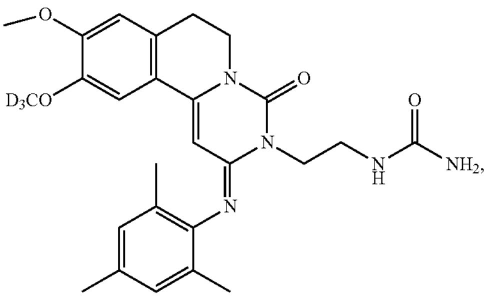

or a pharmaceutically acceptable salt thereof.

16. A method of treating asthma in a human comprising administering to the human in need thereof a compound that has the following structure:

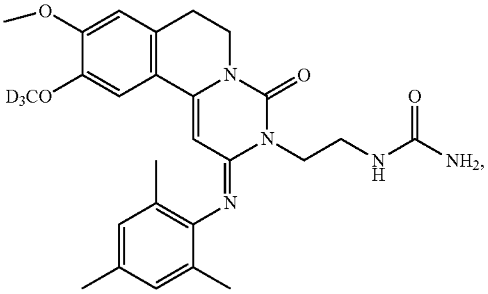

or a pharmaceutically acceptable salt thereof.

17. A method of treating chronic obstructive pulmonary disease (COPD) in a human comprising administering to the human in need thereof a pharmaceutical composition comprising a compound that has the following structure:

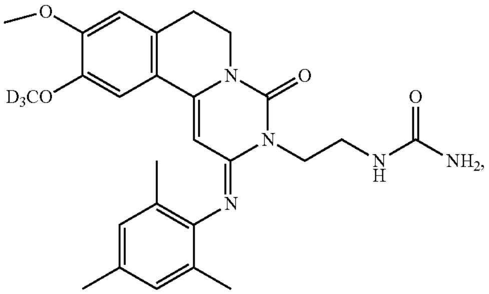

or a pharmaceutically acceptable salt thereof; and a pharmaceutically acceptable carrier and/or auxiliary agent.

18. A method of treating asthma in a human comprising administering to the human in need thereof a pharmaceutical composition comprising a compound that has the following structure:

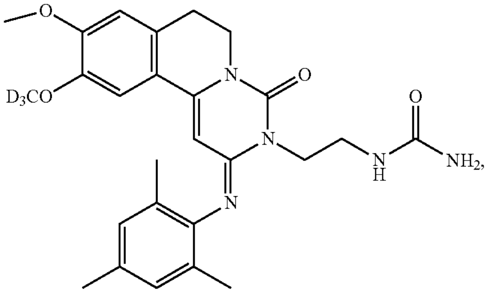

or a pharmaceutically acceptable salt thereof; and a pharmaceutically acceptable carrier and/or auxiliary agent.

* * * * *